(12) United States Patent
Okushi et al.

(10) Patent No.: US 7,833,240 B2
(45) Date of Patent: Nov. 16, 2010

(54) ATHERECTOMY CATHETER

(75) Inventors: Naohisa Okushi, Shizuoka-ken (JP);
Kinya Harada, Shizuoka-ken (JP)

(73) Assignee: Terumo Kabushiki Kaisha,
Shibuya-Ku, Tokyo (JP)

( * ) Notice: Subject to any disclaimer, the term of this patent is extended or adjusted under 35 U.S.C. 154(b) by 647 days.

(21) Appl. No.: 11/714,148

(22) Filed: Mar. 6, 2007

(65) Prior Publication Data

US 2007/0208361 A1    Sep. 6, 2007

(30) Foreign Application Priority Data

Mar. 6, 2006   (JP)   ............... 2006-059961
Jun. 19, 2006  (JP)   ............... 2006-169165

(51) Int. Cl.
*A61B 17/22* (2006.01)
*A61B 17/32* (2006.01)
(52) U.S. Cl. ............... 606/159; 606/170; 606/180
(58) Field of Classification Search ............... 606/108, 606/159, 170, 180, 194, 200; 623/1.11, 1.42, 623/1.46
See application file for complete search history.

(56) References Cited

U.S. PATENT DOCUMENTS 5,074,845 A * 12/1991 Miraki et al. .......... 604/103.08
5,254,107 A * 10/1993 Soltesz ............... 604/525
5,490,859 A *  2/1996 Mische et al. ............ 606/159
6,036,708 A *  3/2000 Sciver ................. 606/159
6,638,268 B2* 10/2003 Niazi ................. 604/528

FOREIGN PATENT DOCUMENTS

NL    1000163        10/1996
WO    WO 94/24946 A1 11/1994
WO    01/74255 A1    10/2001

OTHER PUBLICATIONS

Partial European Search Report for 07004427, dated Jul. 10, 2007.

* cited by examiner

*Primary Examiner*—Anhtuan T Nguyen
*Assistant Examiner*—Ashley Cronin
(74) *Attorney, Agent, or Firm*—Buchanan Ingersoll & Rooney PC

(57) ABSTRACT

An atherectomy catheter includes an outer tube; an inner tube which is inserted into the outer tube rotatably about an axis thereof and axially movably; a removing member fixed to a distal portion of the inner tube and accommodated in the outer tube to drill and remove an occlusive material which stenoses or occludes a lumen of a blood vessel; and a guide member mounted on the inner tube in penetration therethrough so that the guide member functions as the axis of the inner tube when the inner tube rotates. The removing member has a developed state in which a distal end of the removing member unfolds when the removing member is projected from a distal portion of the outer tube and radially expands owing to an elastic restoring force thereof, and the removing member can drill said occlusive material in the developed state by rotating about the guide member functioning as an axis of said removing member and moving the removing member toward a distal end of the atherectomy catheter.

13 Claims, 25 Drawing Sheets

ATHERECTOMY CATHETER

BACKGROUND OF THE INVENTION

The present invention relates to an atherectomy catheter for removing an occlusive material stenosing or occluding lumens of tubular organs.

Atherosclerosis is caused by precipitation of fatty acid inside a lower side of the inner membrane layer of a blood vessel. Conceivably, comparatively soft fatty acid deposits initially at the lower side of the inner membrane layer. With the passage of time, a cholesterol component is captured into the deposited fatty acid to form a calcified atheroma layer. The inside of the blood vessel has a stenosed state or an occluded state owing to the formed atheroma layer. Thereby a bloodstream is interrupted. If this state is left, angina, myocardial infarction occur in the case of the heart, and necrosis of finger tissues of hands and legs and intermittent claudication in the case of the limbs.

Atherectomy means a procedure for removing a developed arteriosclerotic layer from the blood vessel by a catheter. Normally, only the atherectomy is not performed but carried out in combination with a balloon angioplasty. Further to maintain a lumen formed by the removal of the arteriosclerotic layer and the angioplasty, a stent placement is performed. Even if such a procedure is performed, a new arteriosclerotic layer may develop at the inner side of a stent as pointed out in many research reports. In this case, the atherectomy, the balloon angioplasty, and the stent placement are often performed. Recently researches are made to decrease a stenosis rate by the drug eluting stent expected to have the effect of preventing hyperplastic arteriosclerosis.

The atherectomy may be performed to treat chronic occlusion in which a bloodstream is completely interrupted. In some cases, as the amount of the bloodstream becomes smaller, the inner membrane of the blood vessel grows increasingly large. Various techniques for treating these lesions are disclosed.

For example, in the technique disclosed in WO01/74255, the rotor is expandable and contractible. By utilizing the expandability and contractibility of the sheath means functioning as the rotor, the sheath means is repeatedly pushed into a desired portion inside the blood vessel and pulled therefrom until a inner diameter of a blood vessel is dilated.

A thrombus is another cause of occluding the blood vessel. In some cases, the thrombus generated by a bleed of a blood vessel flows to a periphery and deposits thereon. The surface of the atheroma layer is liable to be damaged. Thus when the surface of the atheroma layer is damaged for some reason, platelets in circulating blood may agglutinate to form the thrombus. As a result, the blood vessel is occluded. In some cases, the thrombus is present together with the atheroma layer. Techniques of removing the deposited thrombus by using a balloon have been used for a long time.

In the catheter described in WO01/74255, it is necessary to perform the operation of penetrating the distal end-closed basket-shaped sheath means (shear member) into a lesion of a developed arteriosclerotic layer or a lesion stenosed or occluded with the thrombus. It is also necessary to repeatedly perform the operation of pushing or pulling the sheath means by rotating the sheath means until the inner diameter of the blood vessel is dilated.

But in a lesion close to occlusion or an occluded lesion, it is difficult for a contrast media to flow therein even in an examination by fluoroscopy. Thus it is difficult to discriminate a portion of the lesion to which the sheath means is approached. It is also difficult to correctly penetrate the sheath means through the lesion. Thus the sheath means is liable to damage the blood vessel or break therethrough. As described above, the catheter described in WO01/74255 necessitates an operator to take much time and labor and become skilled.

It is an object of the present invention to provide an atherectomy catheter capable of easily, rapidly, securely, and safely removing an occlusive material from a stenosed or occluded lumen of a tubular organ.

SUMMARY OF THE INVENTION

The object described above is attained by the following an atherectomy catheter.

An atherectomy catheter comprises a flexible outer tube; a flexible inner tube which is inserted into said outer tube rotatably about an axis thereof and axially movably; a removing member fixed to a distal portion of said inner tube and accommodated in said outer tube to drill and remove an occlusive material which stenoses or occludes a lumen of a tubular organ; and a guide member, flexible and long, which penetrates said inner tube so that said guide member functions as said axis of said inner tube when said inner tube rotates, wherein said removing member has a developed state in which a distal end of said removing member unfolds when said removing member is projected from a distal portion of said outer tube and radially expands owing to an elastic restoring force thereof, and said removing member can drill said occlusive material in said developed state by rotating said removing member about said guide member functioning as an axis of said removing member and moving said removing member toward a distal end of said atherectomy catheter.

Further, the first object described above is attained by the following an atherectomy catheter.

An atherectomy catheter comprises a flexible outer tube; a flexible inner tube which is inserted into said outer tube rotatably about an axis thereof and axially movably; first and second removing members fixed to a distal portion of said inner tube and accommodated in said outer tube to drill and remove an occlusive material which stenoses or occludes a lumen of a tubular organ, wherein said first and second removing members project from a distal portion of said outer tube and radially expand, thus having a developed state in which a distal end of each of said first and second removing members unfolds.

BRIEF DESCRIPTION OF THE DRAWINGS

FIG. 3(a) is an enlarged sectional view taken along a line A-A of FIG. 1. FIG. 3(b) is an enlarged sectional view taken along a line B-B of FIG. 1. FIG. 3(c) is an enlarged sectional view taken along a line C-C of FIG. 1. FIG. 3(d) is an enlarged sectional view taken along a line D-D of FIG. 1.

FIG. 15(a) is an enlarged sectional view taken along a line E-E of FIG. 13. FIG. 15(b) is an enlarged sectional view taken along a line F-F of FIG. 13. FIG. 15(c) is an enlarged sectional view taken along a line G-G of FIG. 13. FIG. 15(d) is an enlarged sectional view taken along a line I-I of FIG. 13.

DETAILED DESCRIPTION OF THE PREFERRED EMBODIMENTS

Figure 1:
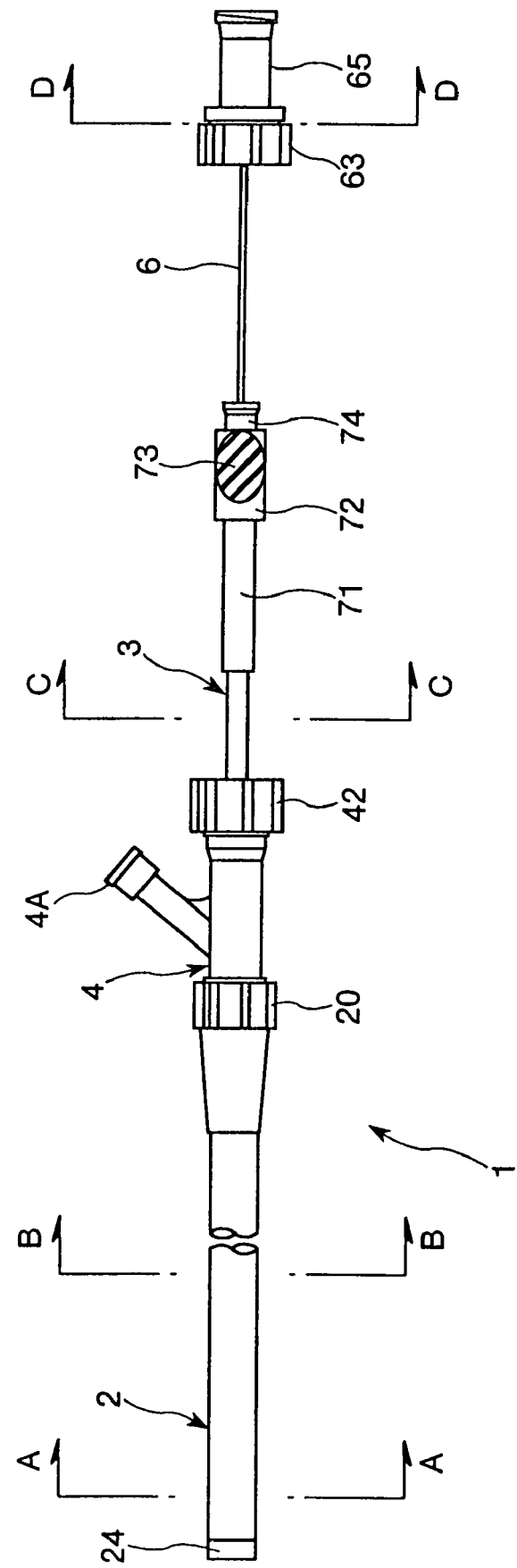
FIG. 1 is a side elevation showing an embodiment of the atherectomy catheter of the present invention.

The atherectomy catheter of the present invention will be described in detail below based on preferred embodiments shown in the drawings.

An atherectomy catheter 1 of the present invention comprises a flexible outer tube 2; a flexible inner tube 3 which is inserted into the outer tube 2 rotatably about an axis thereof and axially movably; a removing member 5 fixed to a distal portion of the inner tube 3 and accommodated in the outer tube 2 to drill and remove an occlusive material which stenoses or occludes a lumen of a tubular organ; and a guide member 6, flexible and long, which penetrates the inner tube 3 so that the guide member 6 functions as the axis of the inner tube 3 when the inner tube 3 rotates.

The removing member 5 has a developed state in which a distal end of the removing member 5 unfolds when the removing member 5 is projected from a distal portion of the outer tube 2 and radially expands owing to an elastic restoring force thereof. The removing member 5 can drill the occlusive material in the developed state by rotating the removing member 5 about the guide member 6 functioning as an axis of the removing member 5 and moving said removing member toward a distal end of the atherectomy catheter 1.

In other words, in removing the occlusive material, the removing member 5 projects from a distal portion of the outer tube 2 and radially expands owing to an elastic restoring force thereof, thus having a developed state in which the distal end of the removing member 5 unfolds; and the guide member 6 projects from a distal portion of the removing member 5 and moves the removing member 5 toward a distal end of the atherectomy catheter 1, with the removing member 5 being rotated about the guide member 6 functioning as an axis of the removing member 5 through the inner tube so that the distal portion of the removing member 5 drills the occlusive material.

In an embodiment which will be described below, the case in which the atherectomy catheter of the present invention is applied to a catheter for removing an occlusive material from stenosed or occluded lumen of a blood vessel.

On the convenience of description, in FIGS. 1, 2, 4 through 12, the left-hand side is set as the "distal end", whereas the right-hand side is set as the "proximal end". FIG. 3 shows only sectional portions of the atherectomy catheter.

An atherectomy catheter (catheter) 1 shown in FIGS. 1 through 12 is a medical device for drilling (destroying or crushing) and removing (to canalise a blood vessel) an unnecessary material generated inside a blood vessel (inside tubular organ) such as the artery to thereby secure a bloodstream. The unnecessary material includes an occlusive material (material occluding blood vessel) stenosing or occluding the lumen of the blood vessel (tubular organ).

As shown in FIG. 1, the atherectomy catheter 1 includes an outer tube 2; a connector 4 provided at a proximal portion of the outer tube 2; an inner tube 3 which is inserted into the outer tube 2 rotatably about an axis thereof and axially movably; a removing member 5 fixed to (mounted on) a distal portion of the inner tube 3 and accommodated in the outer tube 2 to drill and remove an occlusive material which stenoses or occludes a lumen of a blood vessel; and a guide member 6 mounted on the inner tube 3 in penetration therethrough so that the guide member 6 functions as the axis of the inner tube 3 when the inner tube 3 rotates. The atherectomy catheter is hereinafter often referred to as merely "catheter". The occlusive material includes not only unnecessary materials occluding the lumen of the blood vessel, but also various unnecessary materials not completely occluding the lumen but stenosing the lumen. More specifically, the occlusive material includes a thrombus, a fatty plaque, an arteriosclerotic layer, and the like.

Figure 2:
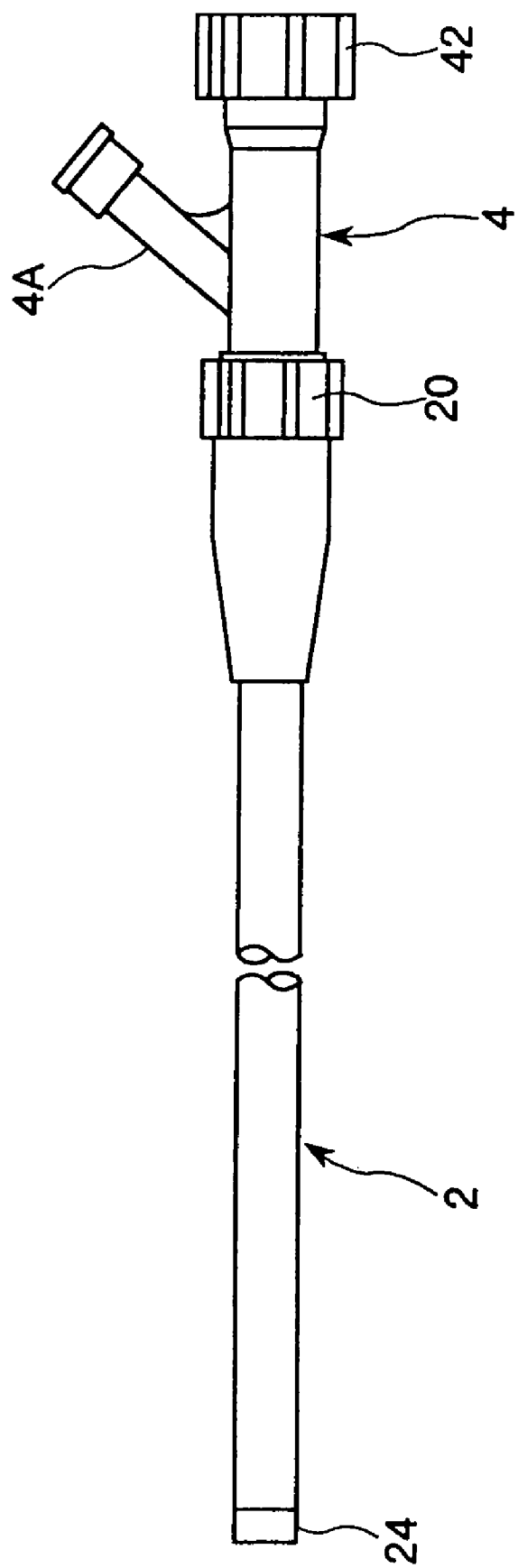
FIG. 2 is a side elevation showing an outer tube having a connector of the atherectomy catheter shown in FIG. 1.
Figure 3:
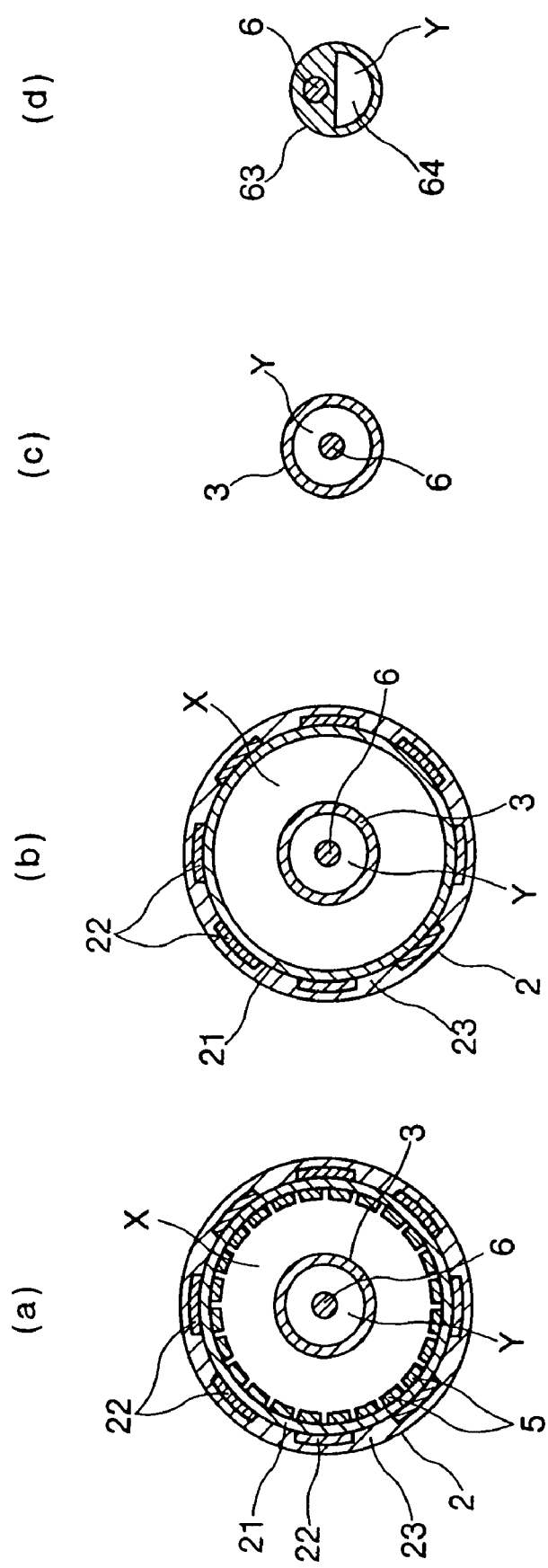
FIG. 3 is an enlarged sectional view showing the atherectomy catheter shown in FIG. 1.

As shown in FIGS. 1 and 2, the outer tube 2 is cylindrical (tubular) and has a certain diameter from its proximal portion to distal portion. As shown in FIGS. 3(a) and 3(b), the outer tube 2 has a three-layer construction composed of an inner layer 21, an intermediate layer 22 formed on the periphery of the inner layer 21, and an outer layer 23 formed on the periphery of the intermediate layer 22. The outer tube 2 is flexible so that it is capable of curving freely along a curve of the blood vessel when the outer tube 2 is inserted thereinto.

The dimension of the outer tube 2 is not specifically limited, but it is preferable to set the outer diameter (diameter) thereof to 1.5 to 3.5 mm, the inner diameter (diameter) thereof to 1.0 to 3.0 mm, and the axial length thereof to 30 to 150 cm.

It is preferable that the inner layer 21 of the outer tube 2 is composed of a low-frictional material. As a material composing the inner layer 21, for example, fluorinated resins such as polytetrafluoroethylene are used.

It is preferable that the intermediate layer 22 of the outer tube 2 has a composition functioning as a reinforcing material. As a material composing the intermediate layer 22, it is possible to list stainless steel, tungsten, nickel, titanium, nickel titanium alloy, nickel cobalt alloy, nickel manganese alloy, and carbon fiber. It is preferable that the intermediate layer 22 is composed of a mesh composed of knitted metal wires of the above-described metals or knitted fibers of carbon fibers or the like.

As a material composing the outer layer 23 of the outer tube 2, it is possible to use the following: polyolefins such as polyethylene, polypropylene, polybutadiene; polyvinyl chloride, polyurethane, polyether polyurethane, ethylene-vinyl acetate copolymer, polyethylene terephthalate, polybutylene terephthalate, polyamide, polyether polyamide, polyester polyamide; thermoplastic elastomers such as styrene, polyolefins, polyurethanes, polyesters, polyamides, polybutadienes, trans-polyisoprenes, fluororubbers, and chlorinated polyethylenes. It is possible to use mixtures of not less than two kinds of these thermoplastic and thermoplastic elastomers or laminates of not less than two kinds thereof.

In removing the occlusive material in the blood vessel, it is preferable to enhance the X-ray opaque of the outer tube 2 at essentially the distal portion thereof so that the distal portion thereof is visible in an examination by fluoroscopy. In this case, it is preferable to add an X-ray-opaque material such as barium sulfate, platinum, gold, tungsten or the like to the above-described material composing the outer layer 23 or provide the distal portion of the outer tube 2 with an X-ray opaque portion composed of the X-ray-opaque material. In the embodiment, as shown in FIGS. 1 and 2, the outer tube 2 is provided with an X-ray opaque portion (marker) 24 at its distal portion.

As shown in FIGS. 3(a) and 3(b), the inner tube 3 is cylindrical (tubular) and has an outer diameter so set that it can be inserted into the outer tube 2. A first passage X is formed between the periphery of the inner tube 3 and the inner periphery of the outer tube 2. The inner tube 3 is also flexible.

As a material composing the inner tube 3, it is possible to list polyesters such as polyether ether ketone, polyethylene terephthalate, and polybutylene terephthalate; polyimide, polyamide, polyether polyamide, polyester polyamide, ABS resin, AS resin, and fluorinated resins such polytetrafluoroethylene. It is possible to use mixtures of not less than two kinds of these materials or laminates of not less than two kinds thereof.

The dimension of the inner tube 3 is not restricted to a specific value, but it is preferable to set the outer diameter (diameter) thereof to 0.8 to 1.8 mm, the inner diameter (diameter) thereof to 0.5 to 1.5 mm, and the axial length thereof to 50 to 170 cm.

Figure 4:
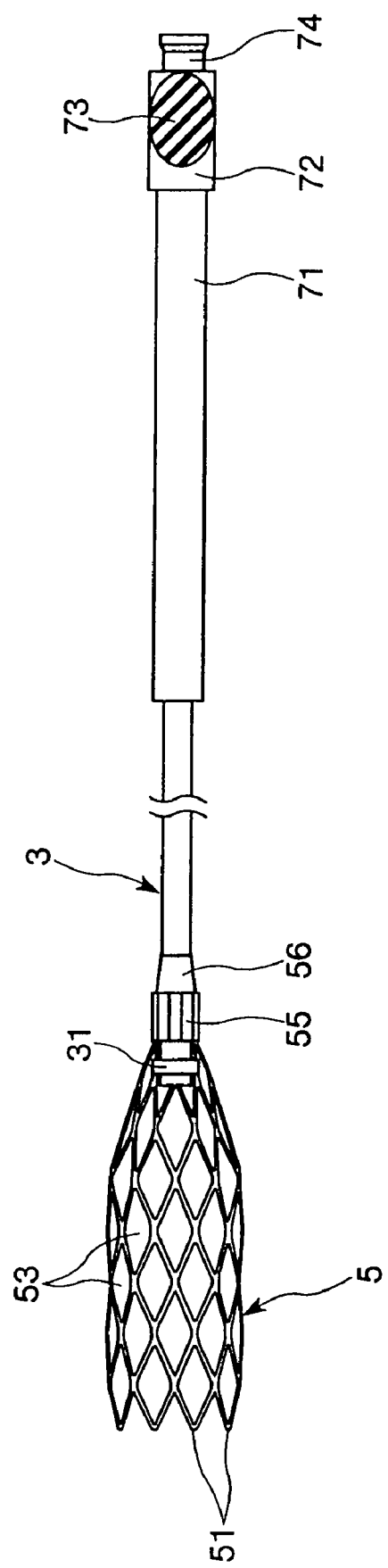
FIG. 4 is a side elevation of an inner tube of the atherectomy catheter shown in FIG. 1 and a removing member thereof.

As shown in FIG. 4, the removing member 5 for drilling and removing the occlusive material generated in the blood vessel is fixed to the distal portion of the inner tube 3 having the above-described construction.

Figure 5:
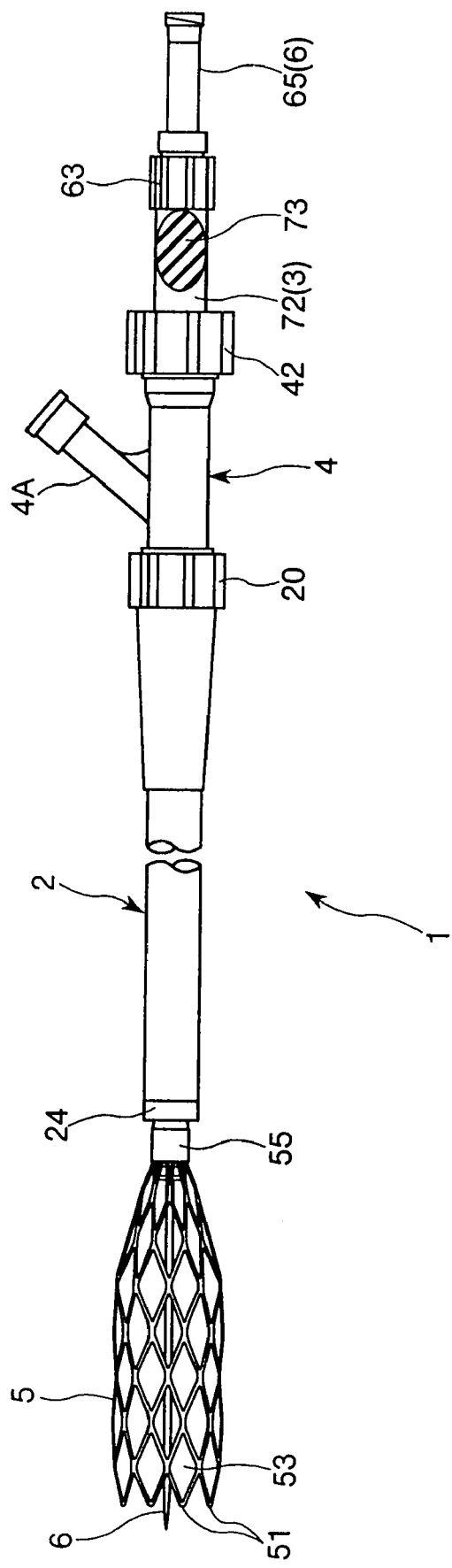
FIG. 5 is a side elevation showing the atherectomy catheter shown in FIG. 1 in which the removing member has a developed state.

The removing member 5 is so constructed that as shown in FIG. 1, the removing member 5 is capable of taking a contracted state (narrowed state) in which it is accommodated in the outer tube 2 (accommodated state) and a developed state in which the removing member 5 projects from the distal portion of the outer tube 2 and radially expands owing to its elastic restoring force, with the distal end thereof unfolding, as shown in FIG. 5. The removing member 5 takes a natural state (state in which no load is applied) in the developed state. In the developed state, the distal portion of the removing member 5 moves away from the guide member 6. In removing the occlusive material, the removing member 5 projects from the distal portion of the outer tube 2 and radially expands owing to its elastic restoring force, thus having the developed state in which the distal end thereof unfolds.

The removing member 5 when it has the developed state is described below representatively.

As shown in FIGS. 4 and 5, the removing member 5 is thin and approximately cylindrical (approximately conic). The removing member 5 has at the distal portion thereof a plurality of projected portions 51 projected circumferentially toward the distal side of the catheter 1. Thereby the removing member 5 is capable of easily and securely drilling the occlusive material.

A side-wall portion of the removing member 5 is reticulate. More specifically, the removing member 5 has a plurality of open portions 53 on a side surface (side wall) thereof. Thereby it is possible to discharge the occlusive material drilled by the removing member 5 through the open portions 53 and inject a predetermined fluid to the blood vessel through the open portions 53.

The ratio of the area of the open portions 53 of the removing member 5 to that of the side surface thereof is set to favorably 4 to 97% and more favorably 20 to 70%.

When the above-described ratio is less than the above-described lower limit value, there is a possibility that the removing member 5 is incapable of expanding by itself in dependence on other conditions.

When the above-described ratio is more than the above-described upper limit value, at the time of drilling, the removing member 5 may twist or change from the developed state to the contracted state in dependence on other conditions.

Each of the open portions 53 is approximately rhombic and thus has a pair of corners in its axial direction. When the removing member 5 is accommodated in the outer tube 2 and thus has the contracted state, each of the open portions 53 so deforms that the angle of a pair of the axial corners thereof becomes small, whereas the angle of the another pair of the corners (a pair of corners approximately vertical to axial direction) thereof becomes large.

When the removing member 5 projects from the distal portion of the outer tube 2, each of the rhombic open portions 53 so deforms that the angle of a pair of the axial corners thereof becomes larger than the angle at the time when the removing member 5 has the contracted state, whereas the angle of the another pair of the corners thereof becomes smaller than the angle at the time when the removing member 5 has the contracted state. Therefore the removing member 5 expands radially, thus having the developed state in which its distal end unfolds (the removing member returns to the natural state).

Owing to the above-described construction, the removing member 5 is capable of taking the developed state smoothly and reliably. The projected portion 51 of the removing member 5 disposed at the distal portion thereof is pointed like the top of a mountain (V-shaped).

As a material composing the removing member 5, it is preferable to use shape memory alloys. As the shape memory alloys, the following can be used: Ti—Ni-based alloys such as Ti—Ni, Ti—Ni—Cu, and the like; a Cu-based alloys such as Cu—Al—Mn, Cu—Al—Ni, and the like; Fe-based alloys such as Fe—Mn—Si and the like; Cd-based alloys such as Au—Cd, Ag—Cd, and the like; ferromagnetic shape memory alloys such as Ni—Mn—Ga alloy, and Fe—Pd alloy.

The dimension of the removing member 5 is not specifically restricted. But it is preferable to set the thickness thereof to 0.1 to 0.3 mm.

Figure 7:
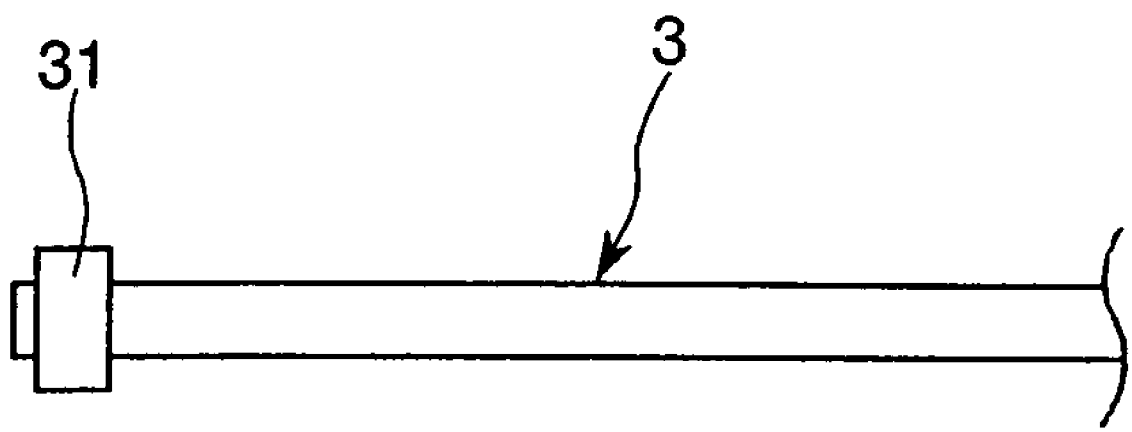
FIG. 7 is a side elevation showing a distal side of the inner tube of the atherectomy catheter shown in FIG. 1.

The method of fixing (sticking) the removing member 5 to the distal portion of the inner tube 3 is not specifically restricted, but the removing member 5 can be fixed to the distal portion of the inner tube 3 as follows:

As shown in FIG. 7, the inner tube 3 having a ring-shaped convex portion 31 provided on the periphery of the distal portion thereof is prepared. In this case, after photo-curing resin is applied to the periphery of the distal portion of the inner tube 3, the photo-curing resin is cured to form the convex portion 31.

Figure 6:
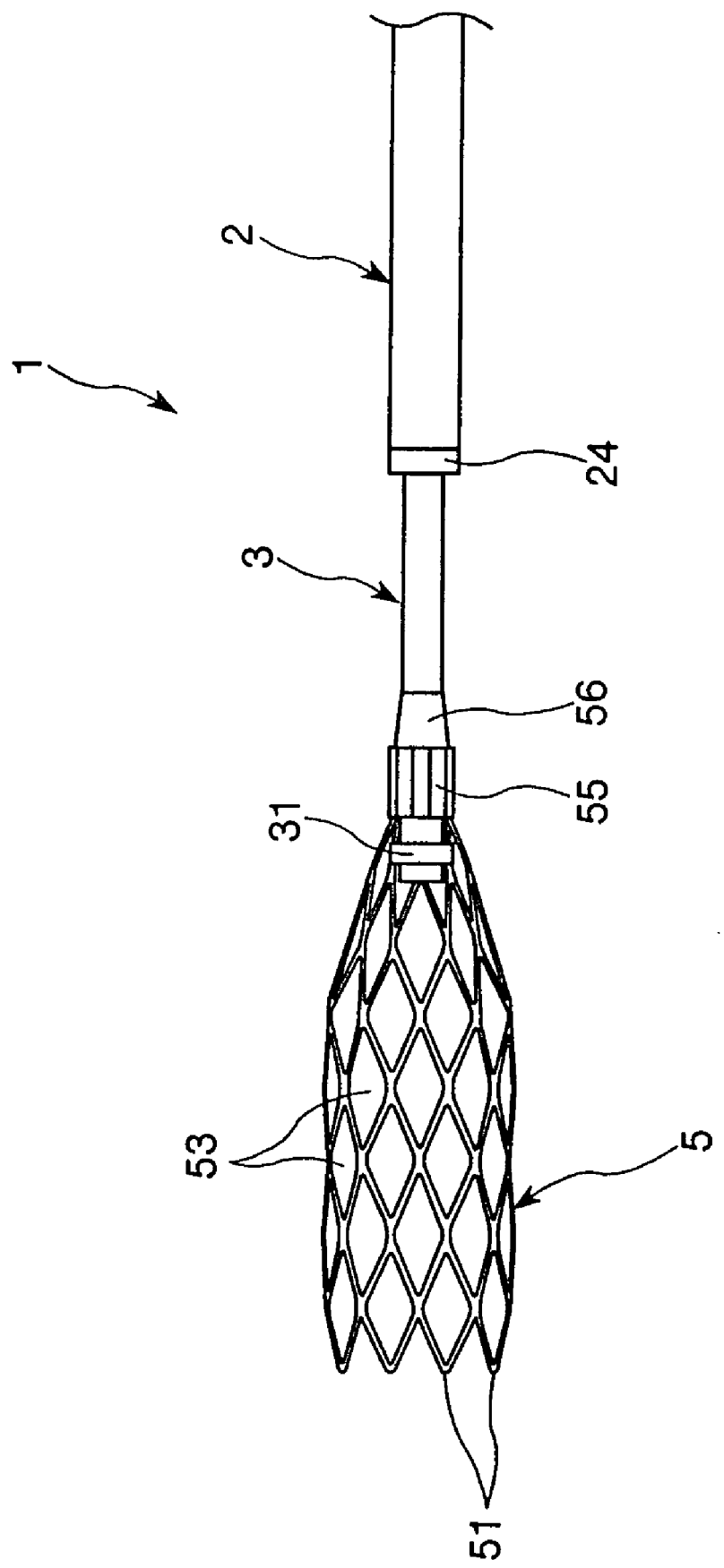
FIG. 6 is a side elevation showing the side of the removing member of the atherectomy catheter shown in FIG. 5.

As shown in FIG. 6, a tubular member 55 to be mounted around the inner tube 3 is prepared. The inner diameter (diameter) of the tubular member 55 is set less than a value obtained by adding a value twice as large as the thickness of the removing member 5 to the outer diameter (diameter) of the convex portion 31. Stainless steel or the like is used as a material composing the tubular member 55.

Figure 8:
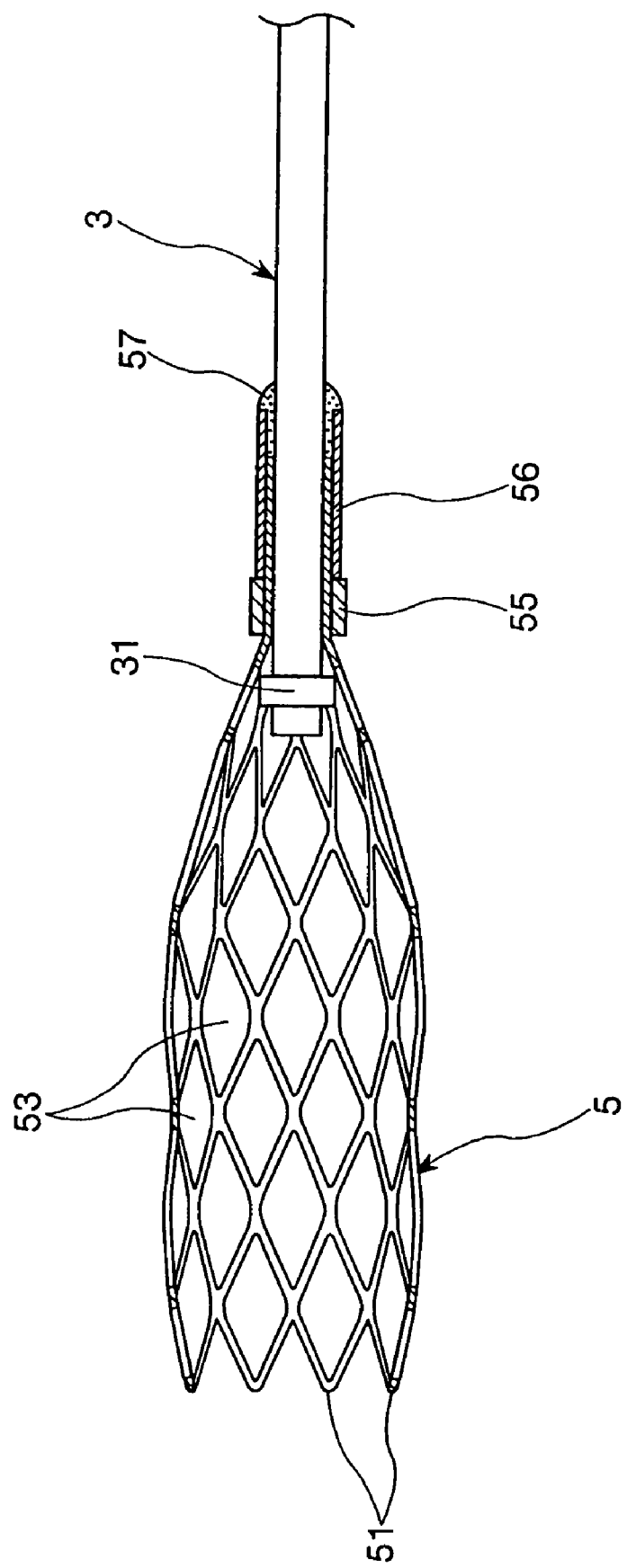
FIG. 8 is a partly sectional view showing a state in which the removing member is fixed to a distal portion of the inner tube shown in FIG. 7.

As shown in FIG. 8, after the removing member 5 is inserted into the tubular member 55 by narrowing the proximal portion of the removing member 5, the inner tube 3 is inserted into the distal portion of the removing member 5 and the tubular member 55 from the proximal side of the inner tube 3. Thereafter, the movement of the tubular member 55 is stopped by bringing it into contact with the convex portion 31. The tubular member 55 is disposed nearer to the proximal side of the atherectomy catheter 1 than the convex portion 31 of the inner tube 3. Thereby the tubular member 55 is placed at a position of the periphery of the inner tube 3 nearer to the proximal side of the atherectomy catheter 1 than the convex portion 31 of the inner tube 3, with the proximal portion of the removing member 5 disposed between the periphery of the inner tube 3 and the inner periphery of the tubular member 55.

After the proximal end of the removing member 5 is projected toward the proximal side of the catheter 1 in a predetermined length from the proximal end of the tubular member 55, a tube 56 is mounted around the proximal portion of the removing member 5. Various resin materials are used as a material composing the tube 56.

After a photo-curing resin 57 is supplied to the periphery of the inner tube 3 toward the distal end thereof from the proximal side of the tube 56 and cured, the tubular member 55 and an end of the removing member 5 are fixed to the inner tube 3. Thereafter the photo-curing resin 57 is applied to the inner tuber 3 to fill a level difference between an end of the tube 56 and the inner tube 3 and cured. By fixing the tubular member 55 to the periphery of the inner tube 3 with the photo-curing resin (adhesive agent) 57, the removing member 5 is fixed to the inner tube 3.

The removing member 5 may be fixed (stuck) to the distal portion of the inner tube 3 by caulking the tubular member 55.

As shown in FIG. 4, as a rotation-assisting means, a pipe 71 is mounted around the proximal portion of the inner tube 3. Thereby the rotation torque transmitting performance of the proximal portion of the inner tube 3 is made larger than that of the distal portion thereof. Thus the inner tube 3 and the removing member 5 can be rotated easily about the axis inside the outer tube 2. Metal materials such as stainless steel are used as a material composing the pipe 71.

The rotation-assisting means does not necessarily have to be constructed of the pipe 71, but may be realized by composing the proximal portion of the inner tube 3 of metal materials such as stainless steel.

An inner-tube hub 72 is provided at the proximal end (proximal portion) of the inner tube 3. The inner-tube hub 72 is provided with a hole (not shown) formed along the axis and a gripping portion 73 formed flatly on the side surface thereof so that the inner-tube hub 72 can be rotated with fingers. Further the inner-tube hub 72 is provided with a coupling portion 74 formed at the proximal side thereof.

As shown in FIG. 2, the connector 4 disposed at the proximal portion of the outer tube 2 is a Y-connector having a port 4A. The first passage X (see FIGS. 3(a) and 3(b)) is formed between the inner periphery of the connector 4 and the periphery of the inner tube 3. That is, the port 4A communicates with the first passage X. The connector 4 is coupled with the proximal portion of the outer tube 2 by tightening a fastening member 20. A first fixing means is provided on the connector 4. The first fixing means has a ring-shaped valve 41 and a plunger (operation portion) 42.

Figure 9:
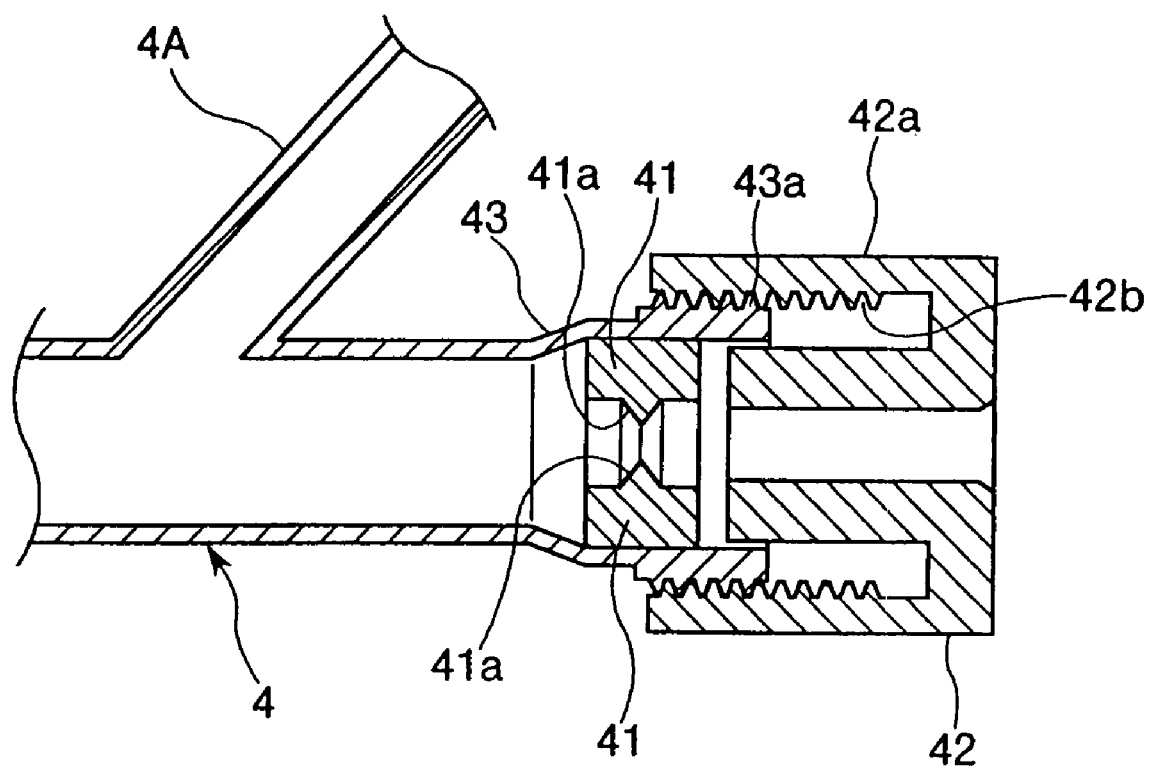
FIG. 9 is a sectional view showing the connector of the atherectomy catheter shown in FIG. 1 and a plunger thereof.

As shown in FIG. 9, a ring-shaped valve 41 is mounted at an inner side of the proximal portion of the connector 4. The connector 4 is provided with a plunger (operation portion) 42 axially movable at the proximal side thereof.

The valve 41 has a rib 41a formed along an inner periphery thereof. The valve 41 is locked to a step region 43 so formed at the proximal portion of the connector 4 that the step region 43 has a larger diameter than the connector 4 to prevent the valve 41 from moving toward the distal side of the connector 4.

On the inner peripheral surface of a peripheral portion 42a of the plunger 42, there is formed a female screw 42b engaging a male screw 43a formed on the peripheral surface of the proximal portion of the connector 4. In this case, by rotating the plunger 42 (operating the plunger 42 to rotate it) in a predetermined direction, the plunger 42 moves toward the distal side of the catheter 1 along the connector 4. Thereby the proximal portion of the connector 4 and the valve 41 are pressed toward the inner tube 3. By rotating the plunger 42 (operating the plunger 42 to rotate it) in the direction opposite to the above-described direction, the plunger 42 moves toward the proximal side of the catheter 1 along the connector 4. Thereby the state in which the proximal portion of the connector 4 and the valve 41 are pressed toward the inner tube 3 is released.

When the proximal portion of the connector 4 and the valve 41 are pressed toward the inner tube 3 owing to the movement of the plunger 42 toward the distal side of the catheter 1, the axial movement of the inner tube 3 with respect to the outer tube 2 is fixed (prevented). At this time, a rotation of the inner tube 3 about the axis relative to the outer tube 2 is permitted, and the valve 41 interrupts (seals) a passage of the fluid through the first passage X.

When the state in which the proximal portion of the connector 4 and the valve 41 are pressed toward the inner tube 3 is released owing to the movement of the plunger 42 toward the proximal side of the catheter 1, the axial movement of the inner tube 3 relative to the outer tube 2 is permitted.

Thus main parts of a first fixing means of the present invention are constructed of the valve 41 and the plunger 42. The first fixing means prevents or fixes an axial movement of the inner tube 3 with respect to the outer tuba.

Figure 10:
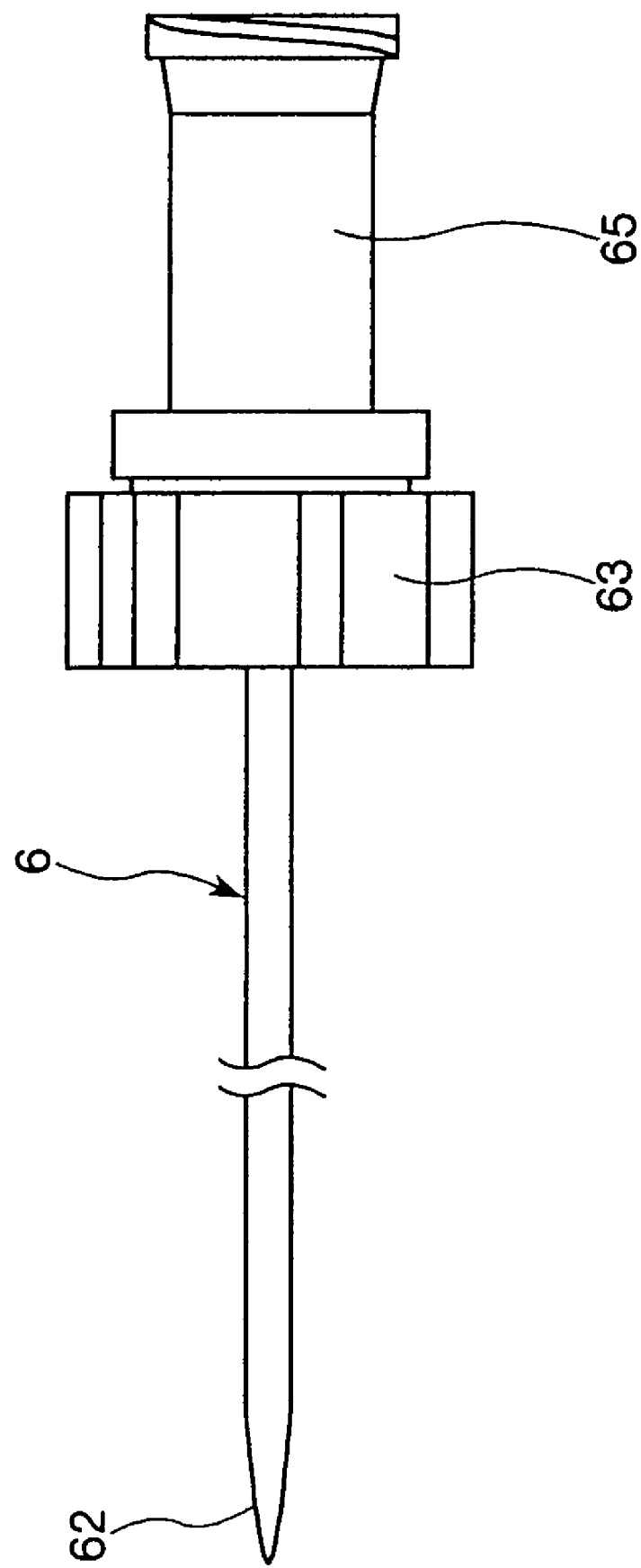
FIG. 10 is a side elevation showing a guide member of the atherectomy catheter shown in FIG. 1.

As shown in FIG. 10, the guide member 6 is flexible and long. That is, the guide member 6 is flexible and linear. In removing the occlusive material, the guide member 6 projects in a predetermined length from the distal portion of the removing member 5. The position of the occlusive material can be specified by striking the guide member 6 against the occlusive material. Further the distal portion of the guide member 6 is pierced into the center of the occlusive material to utilize the guide member 6 as the axis in the rotation of the inner tube 3 and the removing member 5. Thereby it is possible to suppress whirling of the rotational axis of the removing member 5, prevent the wall of the blood vessel from being damaged, and securely remove the occlusive material.

The dimension of the guide member 6 is not specifically limited, but the outer diameter thereof is set to preferably 0.5 to 1.2 mm.

At the distal portion of the guide member 6, there is provided a tapered portion 62 whose outer diameter gradually decreases to its distal end. The distal end of the tapered portion 62 is rounded to allow the tapered portion 62 to be used safely.

In removing the occlusive material in the blood vessel, it is preferable to enhance the X-ray opaque of the guide member 6 at essentially at least the distal portion thereof so that the distal portion thereof is visible in an examination by fluoroscopy. More specifically, it is preferable that at least the distal portion of the guide member 6 is composed of an X-ray opaque material or provided with an X-ray opaque portion (marker).

It is preferable that the guide member 6 is composed of a super-elastic alloy, stainless steel or resin. That is, as a material composing the guide member 6, it is possible to use nickel, titanium, nickel titanium alloy, nickel cobalt alloy, nickel manganese alloy, stainless steel, carbon steel, and resin.

The guide member 6 is removably mounted on the inner tube 3. The atherectomy catheter 1 has a second fixing means for fixing the guide member 6 to the inner tube 3. As shown in FIGS. 1 and 5, the guide member 6 is removable from the inner tube 3. The guide member 6 is provided with a guide hub 63 at its proximal portion. The guide member 6 is fixedly mounted on the inner tube 3 by inserting the guide member 6 into the inner tube 3 and fitting the guide hub 63 on the coupling portion 74 of the inner-tube hub 72 of the inner tube 3.

Thus the main part of the second fixing means of the present invention is constructed of the guide hub 63 and the inner-tube hub 72.

The distal side of the guide member 6 projects in a predetermined length from the distal end of the removing member 5, when the guide member 6 is mounted on the inner tube 3, with the guide hub 63 fitting on the coupling portion 74 of the inner-tube hub 72. The predetermined projected length of the guide member 6 is favorably 1 to 8 mm and more favorably 2 to 5 mm.

By setting the predetermined projected length of the distal side of the guide member 6 to the above-described range, it is possible to keep the guide member 6 safe and securely function the guide member 6 as the axis of the inner tube 3 and the removing member 5 when they rotate.

As shown in FIG. 3(d), a lumen 64 is formed inside the guide hub 63. The lumen 64 is approximately semicircular in its cross-sectional configuration and axially penetrates therethrough. When the guide hub 63 fits on the inner-tube hub 72 of the inner tube 3, the lumen of the inner tube 3, that of the inner-tube hub 72, and the lumen 64 of the guide hub 63 communicate with one another. A second passage Y is composed of these lumens.

A coupling portion 65 is provided at the proximal portion of the guide hub 63.

The atherectomy catheter 1 has unshown connectable rotation-assisting device for rotating the inner tube 3, the removing member 5, and the guide member 6. The rotation-assisting device can be connected with the coupling portion 65 of the guide hub 63.

It is possible to discharge a fluid containing the occlusive material drilled by the removing member 5 to the outside of a human body through the first passage X and inject a predetermined fluid into the blood vessel through the second passage Y.

In this case, a discharge portion of an unshown injection and discharge apparatus (injection and discharge means) is connected with the port 4A of the connector 4. An injection portion of the injection and discharge apparatus is connected with the coupling portion 65 of the guide hub 63.

The fluid containing the occlusive material drilled by the removing member 5 is aspirated and discharged by the operation (drive) of the discharge portion of the injection and discharge apparatus. At this time, it is possible to adjust the flow rate of the fluid, namely, the flow rate per unit time.

The predetermined fluid is injected to the blood vessel by the operation (drive) of the injection portion of the injection and discharge apparatus. At this time, it is possible to adjust the flow rate of the fluid, namely, the flow rate per unit time.

The operation (one example of method of using atherectomy catheter 1) of the atherectomy catheter 1 is described below.

In performing treatment of removing the occlusive material in the blood vessel, the inner tube 3 to which the removing member 5 has been fixed is inserted into the outer tube 2 and accommodated inside the outer tube 2 at the distal side thereof, with the diameter of the removing member 5 decreased. The inner tube 3 and the outer tube 2 are inserted into the blood vessel until the inner tube 3 and the outer tube 2 reach a desired portion in the blood vessel by operating a guide wire (not shown) through a sheath (not shown). The situation at that time is monitored by using fluoroscopic apparatus or the like.

When the inner tube 3 and the outer tube 2 have reached the desired portion of the blood vessel, the guide wire is pulled out of the blood vessel. Thereafter the guide member 6 is inserted into the inner tube 3 from the distal end thereof to fit the guide hub 63 of the guide member 6 on the inner-tube hub 72. Thereby the guide member 6 is fixed to the inner tube 3.

Figure 11:
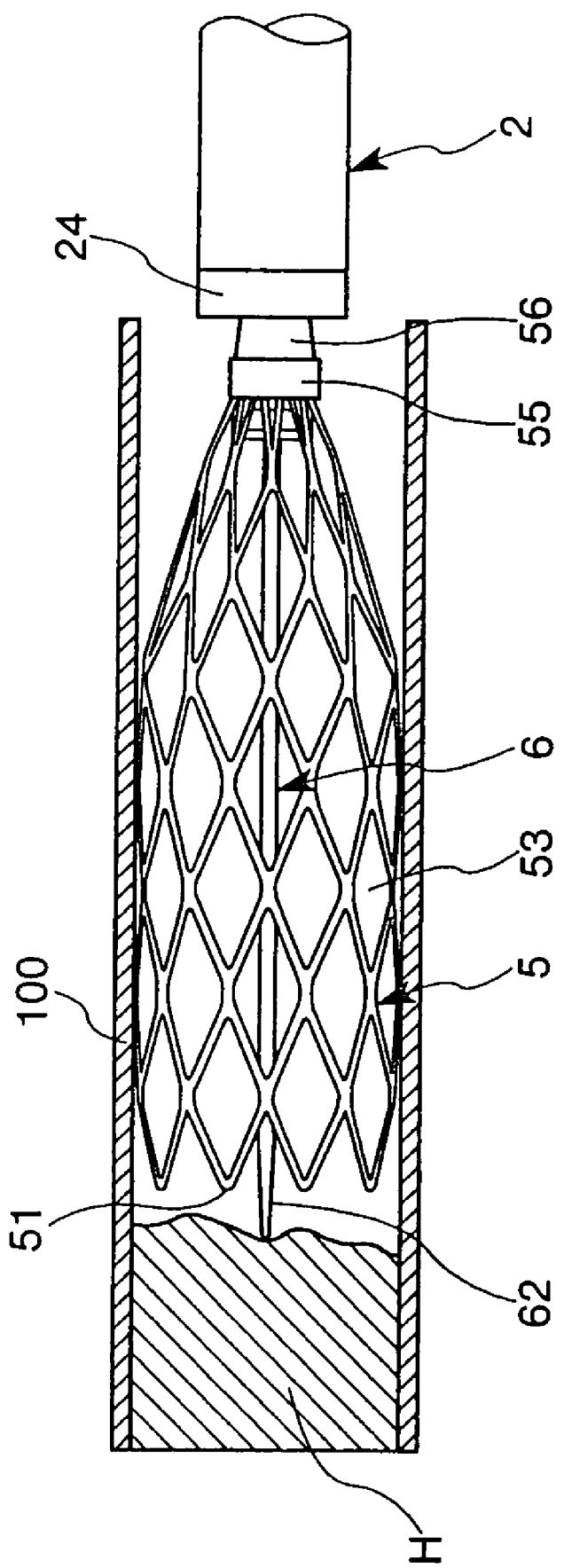
FIG. 11 shows a state in which the guide member of the atherectomy catheter shown in FIG. 5 has struck an occlusive material.
Figure 12:
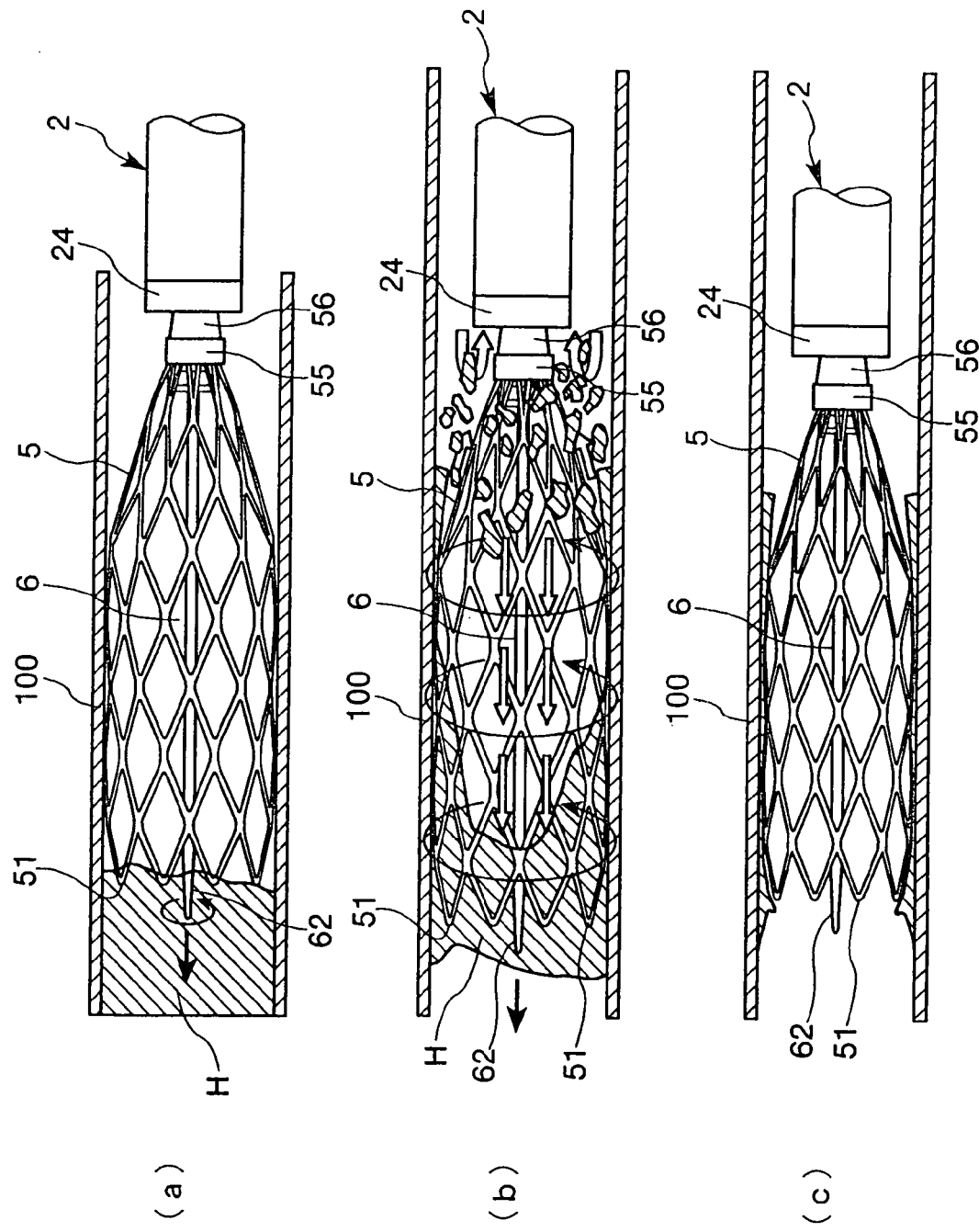
FIG. 12 is an explanatory view showing the operation (until removing member removes occlusive material) of the atherectomy catheter shown in FIG. 5.

Thereafter the plunger 42 of the connector 4 is rotated to loosen the valve 41. In this state, the inner tube 3 is pressed toward the distal side of the outer tube 2. Thereby as shown in FIG. 11, the removing member 5 projects from the distal portion of the outer tube 2 and expands radially owing to its elastic restoring force, thus having the developed state in which the distal end of the removing member 5 unfolds. At this time, the guide member 6 projects in the predetermined length from the distal end of the removing member 5. As a result, the distal portion of the guide member 6 contacts an occlusive material (lesion) H. Thereafter the plunger 42 of the connector 4 is rotated to tighten the valve 41 inward so that the inner tube 3 is rotatably fixed to the outer tube 2.

Thereafter as shown in FIG. 12(a), the atherectomy catheter 1 is entirely moved to the distal side thereof to move the guide member 6 forward so that the distal portion of the guide member 6 is pierced into the occlusive material H inside the blood vessel. Thereafter the inner tube 3 is rotated about the guide member 6 functioning as the axis thereof. Thereby the removing member 5 moves to the distal side of the catheter 1, while the removing member 5 is rotating about the guide member 6 functioning as the axis thereof (axis rotating together with removing member 5).

Thereby as shown in FIG. 12(b), as the guide member 6 enters the occlusive material H, the projected portion 51 of the removing member 5 disposed at the distal portion thereof drills the occlusive material H.

Owing to the forward movement and rotation of the guide member 6 and the removing member 5, as shown in FIG. 12(c), the removing member 5 is securely capable of removing the occlusive material H. In this case, even though the occlusive material H is a hard atheroma such as calcified lesion generated in the blood vessel, the occlusive material H can be securely drilled and removed.

The removed occlusive material H is discharged to the outside through the first passage X.

As described above, according to the atherectomy catheter 1, the removing member 5 is moved to the lesion, of the blood vessel, at which the removing member 5 strikes the occlusive material H inside the blood vessel. At this time, the removing member 5 is moved to the distal side of the catheter 1, with the removing member 5 being rotated. Thereby atherectomy catheter 1 gradually drill and remove the occlusive material H at the projected portion 51 of the removing member 5. Therefore unlike the conventional art, it is unnecessary to perform the operation of penetrating the guide wire through the lesion and repeatedly move the guide wire back and forth. Thus the atherectomy catheter 1 is capable of drilling and removing the occlusive material H easily, rapidly, and securely.

Further because the removing member 5 rotates about the guide member 6 functioning as the axis thereof, the removing member 5 can be rotated easily, securely, and stably.

Therefore without damaging or breaking through the blood vessel and requiring skill, the occlusive material H can be removed easily, rapidly, securely, and safely.

Furthermore because the drilled occlusive material H is discharged to the outside through the first passage X, the atherectomy catheter 1 is very safe.

In removing the occlusive material H, the drilled occlusive material H is discharged to the outside through the first passage X, and physiologic saline or the like can be injected into the blood vessel from the second passage Y. This construction allows the removal of the occlusive material H to be continued without contracting or deforming the blood vessel by a pressure difference generated by aspirating of the drilled occlusive material H in discharging the occlusive material H to the outside.

As described above, because the occlusive material H can be removed, it is possible to secure a bloodstream through the blood vessel and form a way for a device to be used subsequently to the atherectomy catheter 1. In addition, it is possible to perform a subsequent treatment step (expansion of blood vessel with balloon, stent, and the like).

The present invention is not limited to the above-described embodiment of the atherectomy catheter described with reference to the drawings. The construction of each part can be replaced with arbitrary constructions having functions similar to that of each part. In addition, other arbitrary component parts can be added to the present invention.

Portions from which the occlusive material can be removed by the atherectomy catheter of the present invention include the bile duct, the urethra, and the like in addition to the blood vessel.

The occlusive material includes a thrombus, a fatty plaque, an arteriosclerotic layer, a calculus, and the like.

According to the atherectomy catheter of this embodiment in removing the occlusive material, the removing member expands radially and has the developed state in which the distal end of the removing member unfolds. Thus by rotating the removing member with the removing member moving forward, it is possible to drill and remove the occlusive material stenosing or occluding the lumen of a tubular organ (for example, blood vessel) easily, rapidly, and securely.

Because the removing member rotates about the guide member functioning as the axis thereof, the removing member can be rotated easily, securely, and stably.

Therefore without damaging or breaking through the tubular organ and requiring skill, the occlusive material can be removed easily, rapidly, securely, and safely.

An atherectomy catheter of another example of the present invention is described in detail below based on a preferred embodiment shown in attached drawings.

The atherectomy catheter 10 comprises a flexible outer tube 2, a flexible inner tube 3 which is inserted into said outer tube rotatably about an axis thereof and axially movably, first and second removing members 5a and 5b fixed to a distal portion of the inner tube 3 and accommodated in the outer tube 2 to drill and remove an occlusive material which stenoses or occludes a lumen of a tubular organ, wherein first and second removing members 5a and 5b project from a distal portion of the outer tube 2 and radially expand, thus having a developed state in which a distal end of each of first and second removing members 5a and 5b unfolds.

In this embodiment, description is made on the case in which the atherectomy catheter of the present invention is applied to a catheter for removing an occlusive material stenosing or occluding a lumen of a blood vessel.

Figure 13:
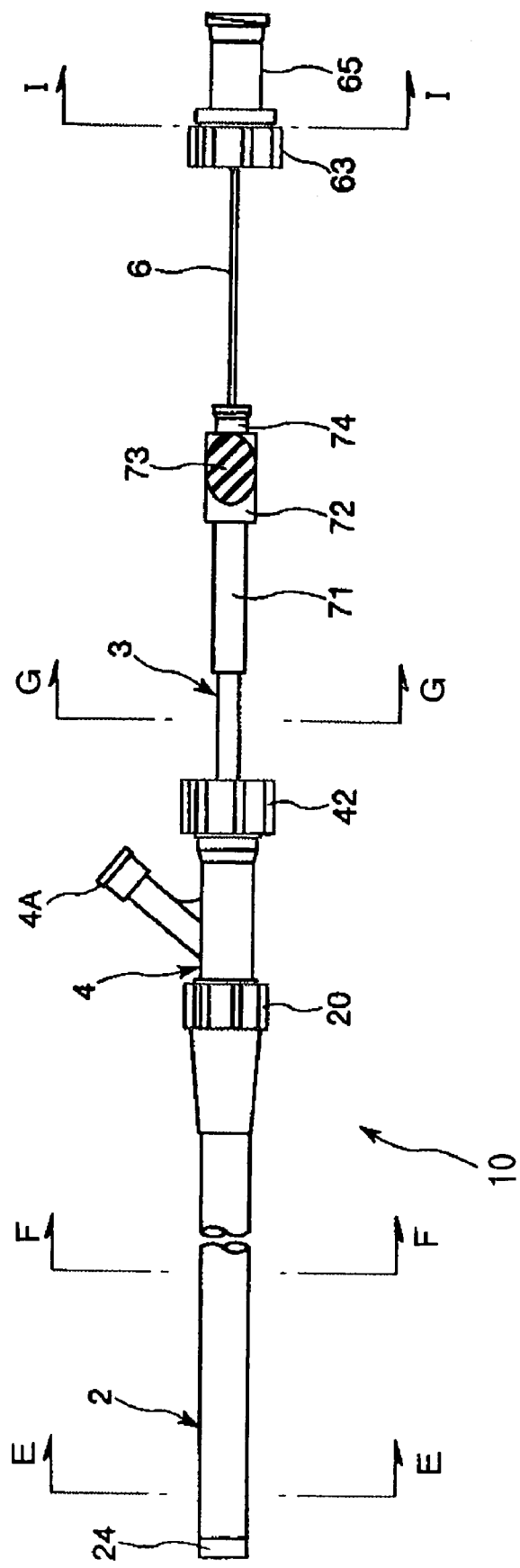
FIG. 13 is a side elevation showing another embodiment of the atherectomy catheter of the present invention.
Figure 14:
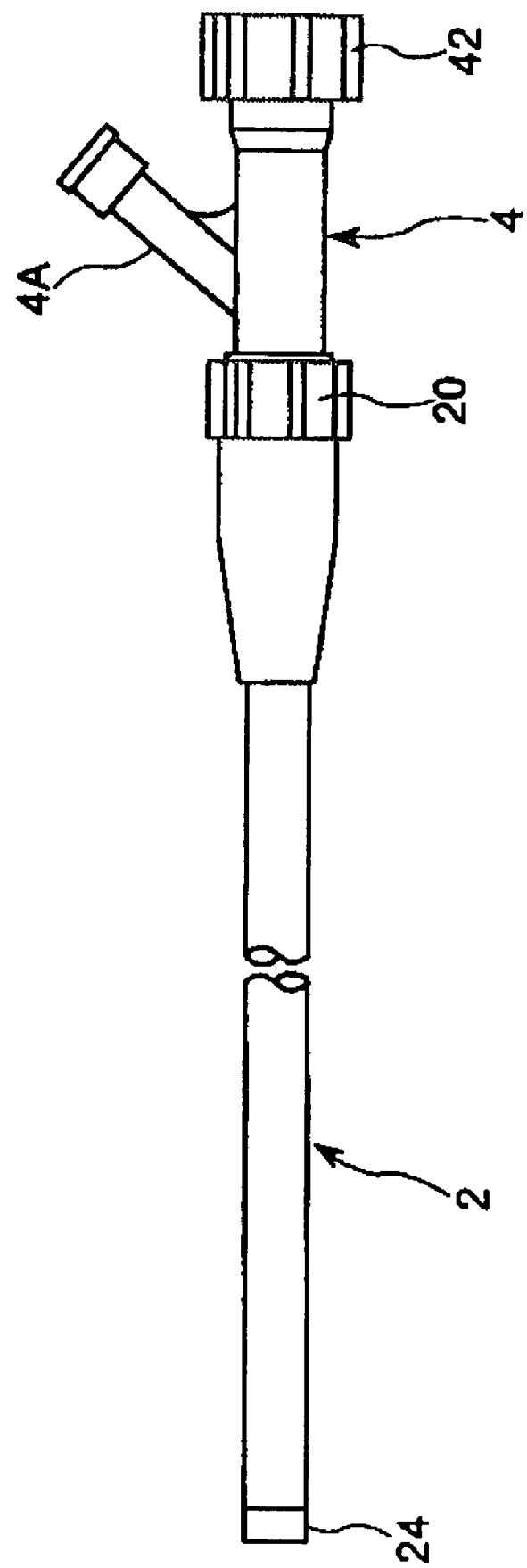
FIG. 14 is a side elevation showing an outer tube having a connector of the atherectomy catheter shown in FIG. 13.
Figure 15:
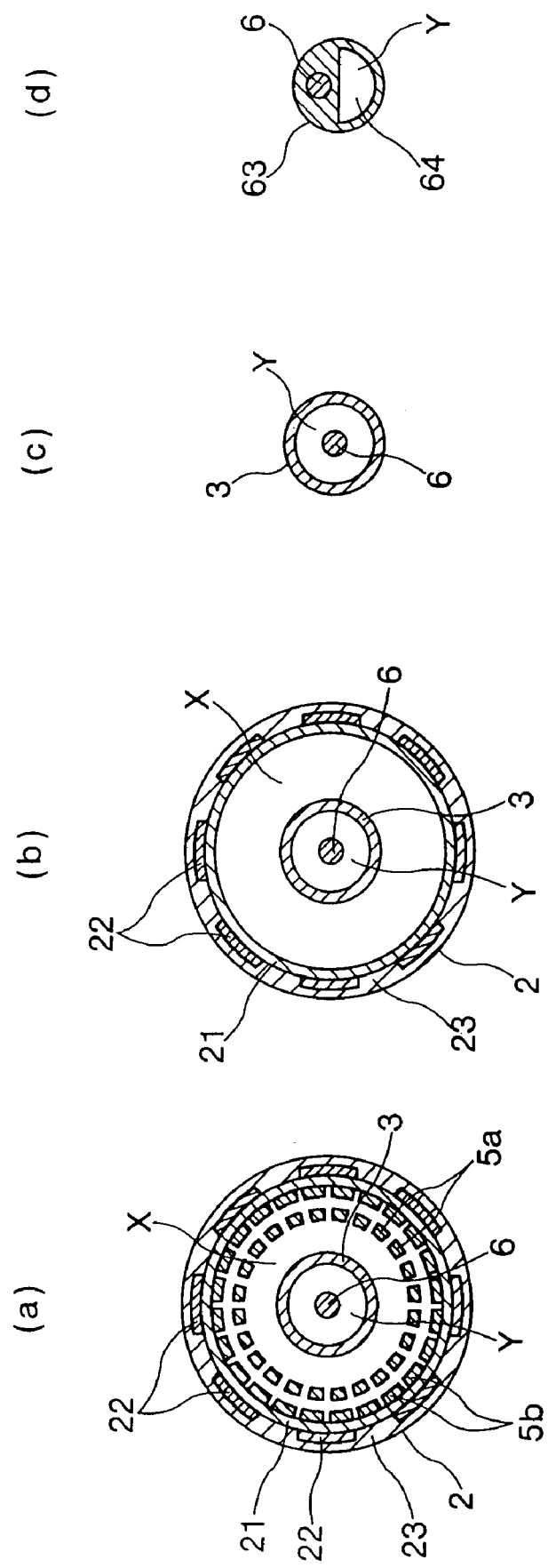
FIG. 15 is an enlarged sectional view showing the atherectomy catheter shown in FIG. 13.
Figure 16:
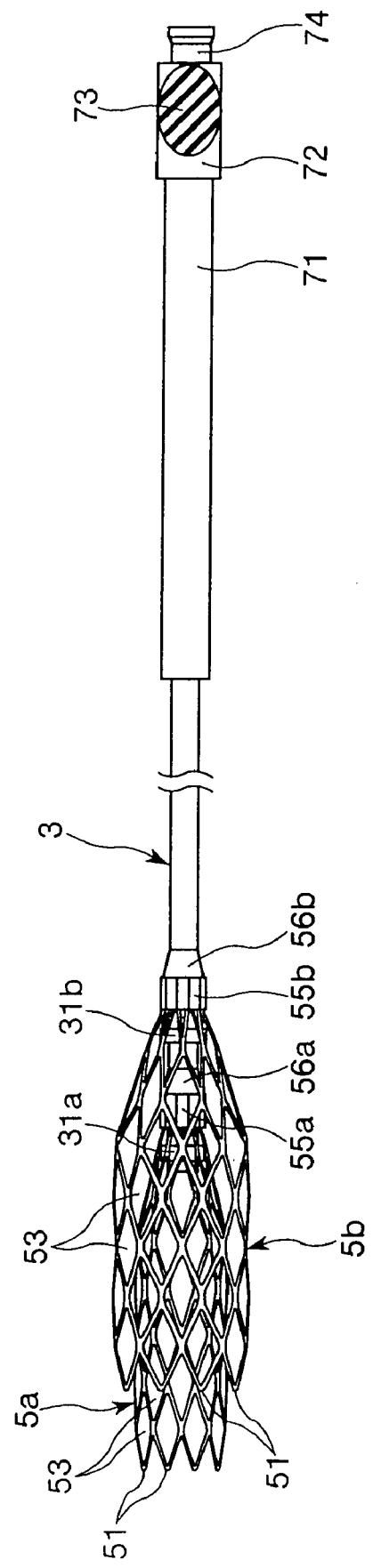
FIG. 16 is a side elevation showing an inner tube and first and second removing members of the atherectomy catheter shown in FIG. 13.
Figure 17:
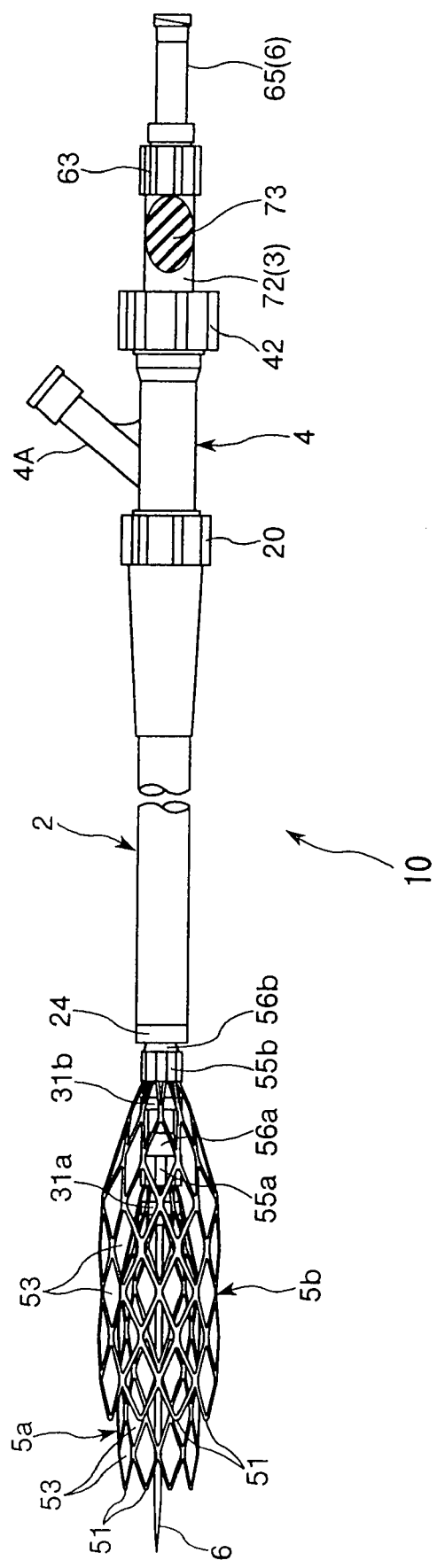
FIG. 17 is a side elevation showing a state in which the first and second removing members of the atherectomy catheter shown in FIG. 13 have a developed state.
Figure 18:
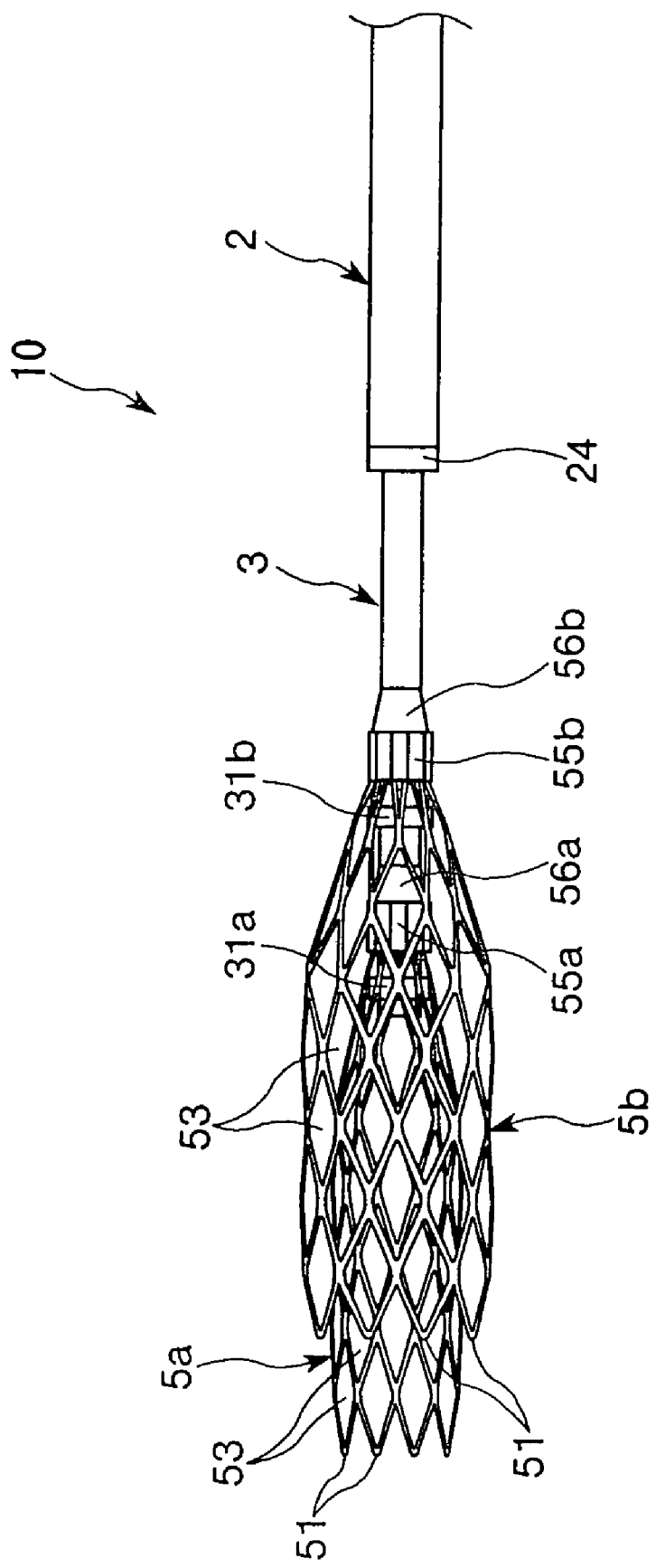
FIG. 18 is a side elevation showing the side of the atherectomy catheter, shown in FIG. 17, where the first and second removing members are disposed.
Figure 19:
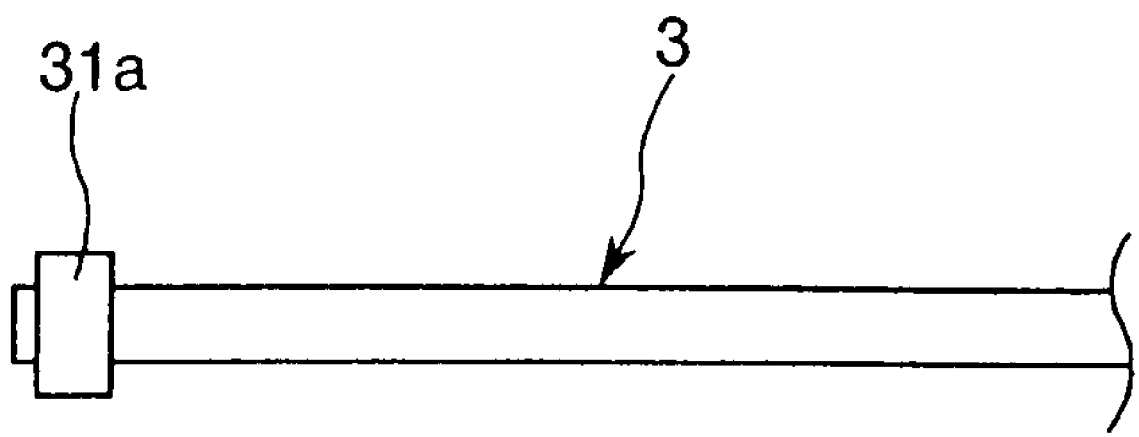
FIG. 19 is a side elevation showing a distal side of the inner tube (before second convex portion is formed) of the atherectomy catheter shown in FIG. 13.
Figure 20:
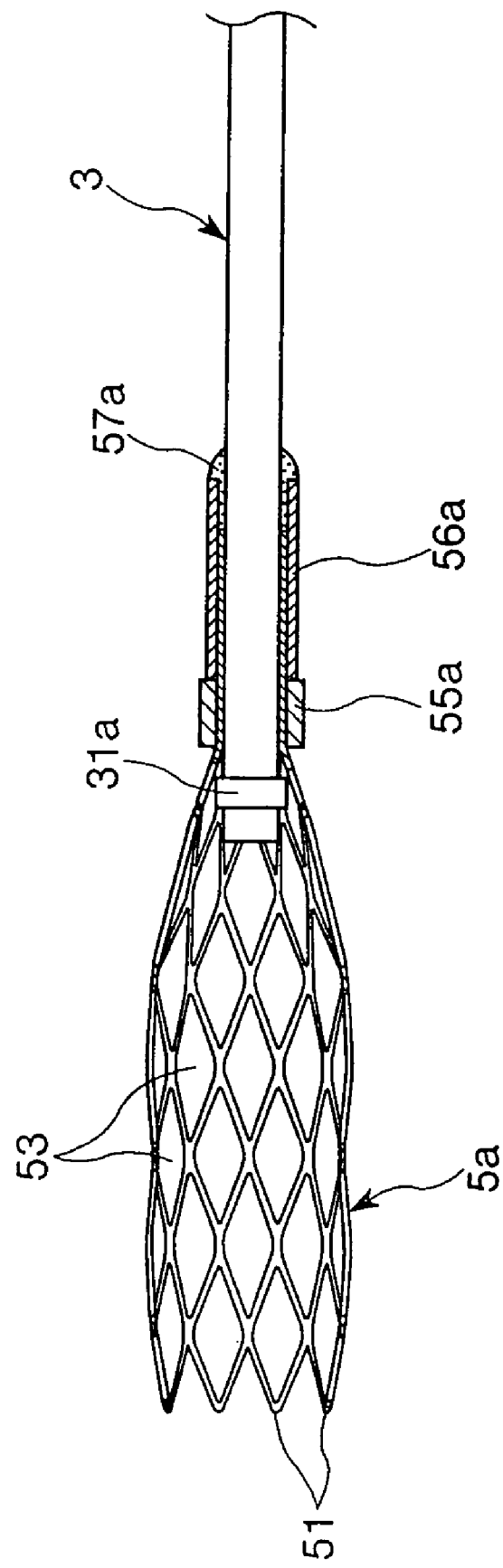
FIG. 20 is a partly sectional view showing a state in which the first removing member is fixed to a distal portion of the inner tube.
Figure 21:
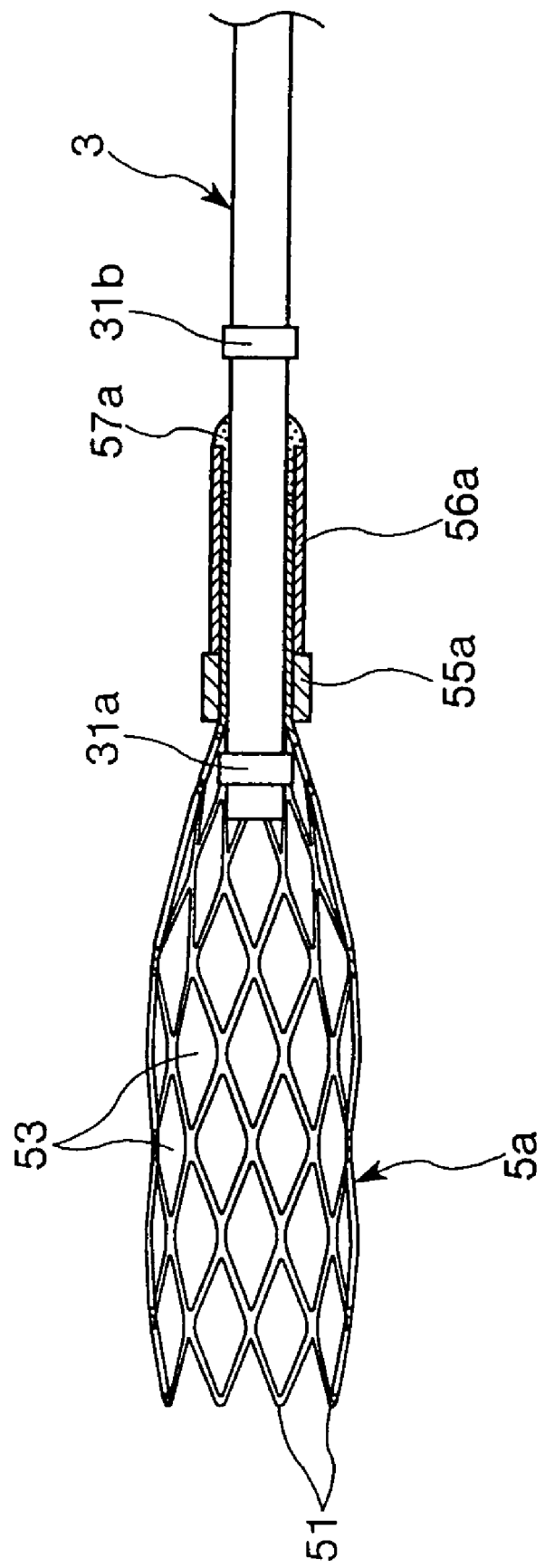
FIG. 21 a partly sectional view showing a state in which a second convex portion is formed at the distal portion, of the inner tube, to which the first removing member is fixed.
Figure 22:
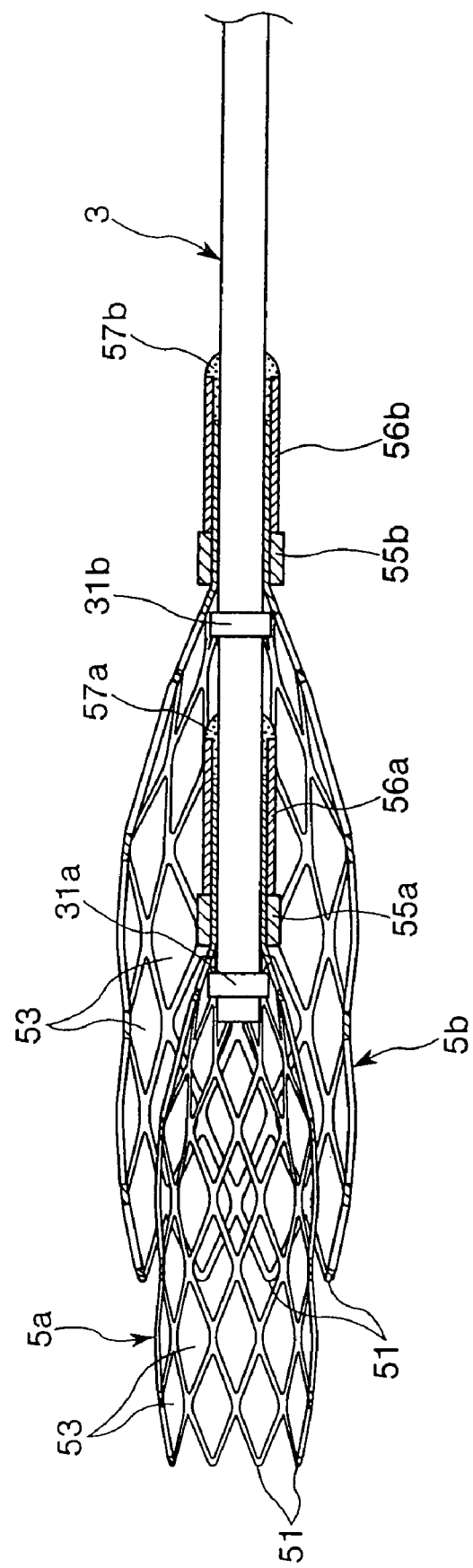
FIG. 22 is a partly sectional view showing a state in which the first and second removing members are fixed to the distal portion of the inner tube.
Figure 23:
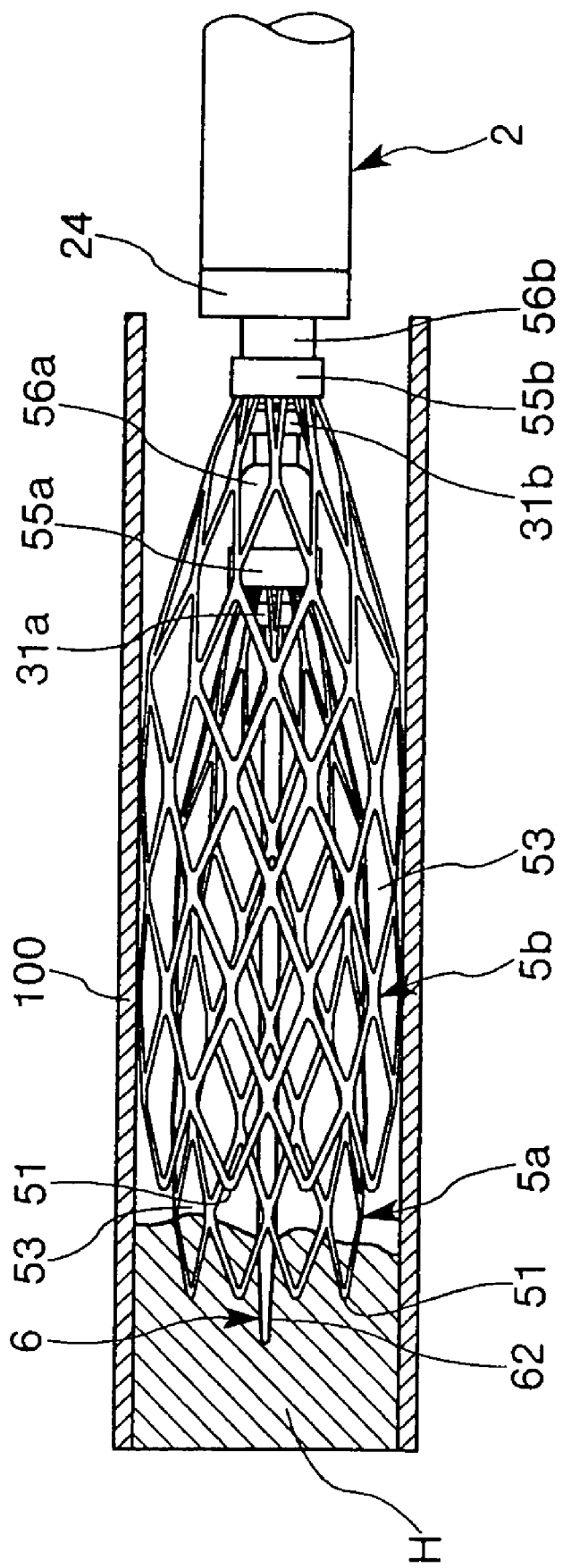
FIG. 23 shows a state in which a guide member of the atherectomy catheter shown in FIG. 17 has struck an occlusive material.
Figure 24:
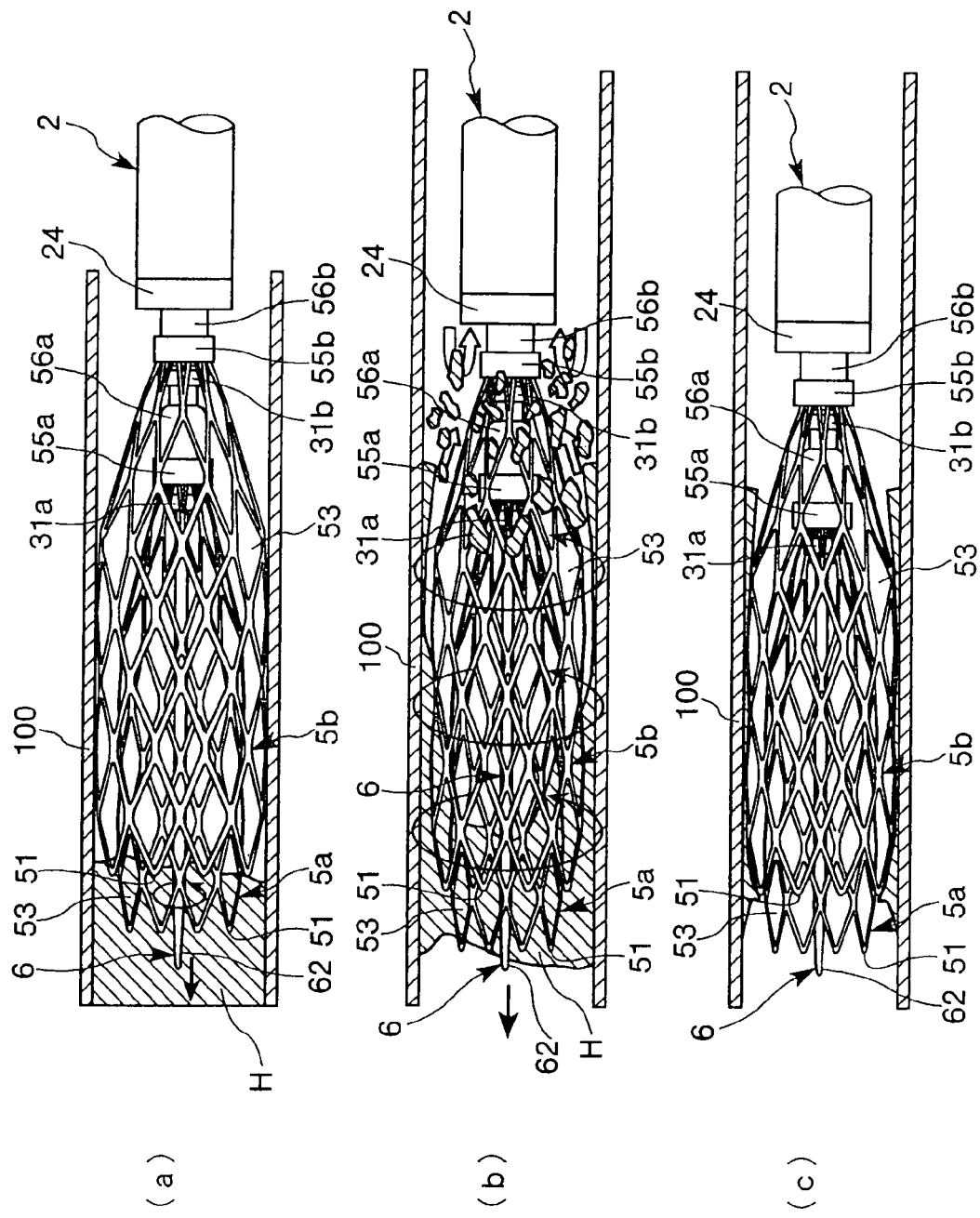
FIG. 24 is an explanatory view showing the operation (until first and second removing members remove occlusive material) of the atherectomy catheter shown in FIG. 17.
Figure 25:
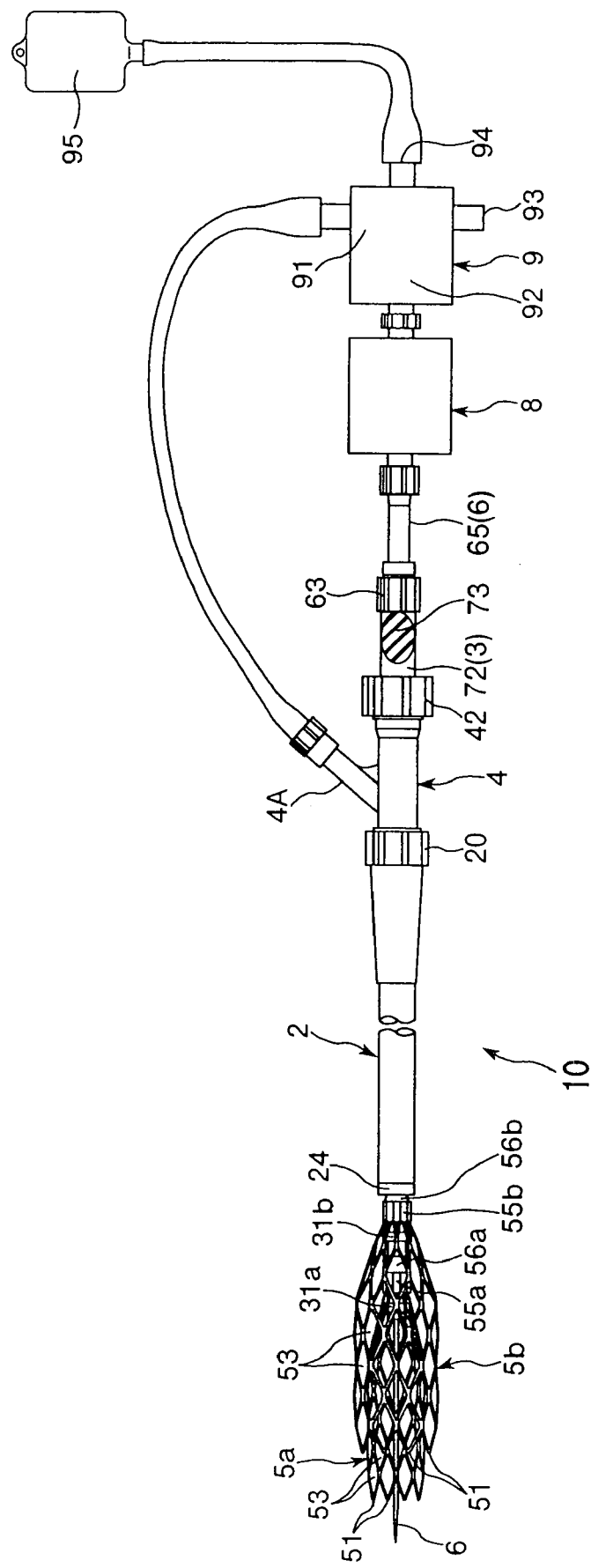
FIG. 25 is a side elevation showing a state in which a rotation-assisting device and an injection and discharge apparatus are connected with the atherectomy catheter.

FIG. 13 is a side elevation showing another embodiment of the atherectomy catheter of the present invention. FIG. 14 is a side elevation showing an outer tube, an outer tube of a connector, and the connector of the atherectomy catheter shown in FIG. 13. FIG. 15 is an enlarged sectional view showing the atherectomy catheter shown in FIG. 13, in which FIG. 15(a) is an enlarged sectional view taken along a line E-E in FIG. 13; FIG. 15(b) is an enlarged sectional view taken along a line F-F in FIG. 13; FIG. 15(c) is an enlarged sectional view taken along a line G-G in FIG. 13; and FIG. 15(d) is an enlarged sectional view taken along a line I-I in FIG. 13. FIG. 16 is a side elevation showing an inner tube and first and second removing members of the atherectomy catheter shown in FIG. 13. FIG. 17 is a side elevation showing a state in which the first and second removing members of the atherectomy catheter shown in FIG. 13 have a developed state. FIG. 18 is a side elevation showing the side of the atherectomy catheter, shown in FIG. 17, where the first and second removing members are disposed. FIG. 19 is a side elevation showing a distal side of the inner tube (before second convex portion is formed) of the atherectomy catheter shown in FIG. 13. FIG. 20 is a partly sectional view showing a state in which the first removing member is fixed to a distal portion of the inner tube. FIG. 21 a partly sectional view showing a state in which a second convex portion is formed at the distal portion, of the inner tube, to which the first removing member is fixed. FIG. 22 is a partly sectional view showing a state in which the first and second removing members are fixed to the distal portion of the inner tube. FIG. 23 shows a state in which a guide member of the atherectomy catheter shown in FIG. 17 has struck an occlusive material. FIG. 24 is an explanatory view showing the operation (until first and second removing members remove occlusive material) of the atherectomy catheter shown in FIG. 17. FIG. 24(a) shows a state in which the first and second removing members have struck the occlusive material. FIG. 24(b) shows a state in which the first and second removing members are drilling and removing the occlusive material. FIG. 24(c) shows a state in which the first and second removing members have removed most of the occlusive material. FIG. 25 is a side elevation showing a state in which a rotation-assisting device and an injection and discharge apparatus are connected with the atherectomy catheter.

On the convenience of description, in FIGS. 13, 14, 16 through 25, the left-hand side is set as the "distal end", whereas the right-hand side is set as the "proximal end". FIG. 15 shows only sectional portions of the atherectomy catheter.

An atherectomy catheter (catheter) 10 shown in FIGS. 13 through 25 is a medical device for drilling (destroying or crushing) and removing (to canalise blood vessel) an unnecessary material generated inside a blood vessel (inside tubular organ) such as the artery to thereby secure a bloodstream. The unnecessary material includes an occlusive material (material occluding blood vessel) stenosing or occluding the lumen of the blood vessel (tubular organ).

As shown in FIG. 13, the atherectomy catheter 10 includes an outer tube 2; a connector 4 provided at a proximal portion of the outer tube 2; an inner tube 3 which is inserted into the outer tube 2 rotatably about an axis thereof and axially movably; a first removing member 5a and a second removing member 5b fixed to (mounted on) a distal portion of the inner tube 3 and accommodated in the outer tube 2 to drill and remove an occlusive material which stenoses or occludes a lumen of a blood vessel. The atherectomy catheter is hereinafter often referred to as merely "catheter". The occlusive material includes not only unnecessary materials occluding the lumen of the blood vessel, but also various unnecessary materials not completely occluding the lumen but stenosing the lumen. More specifically, the occlusive material includes a thrombus, a fatty plaque, an arteriosclerotic layer, and the like. The atherectomy catheter of this embodiment includes a guide member 6, mounted on the inner tube 3 in penetration therethrough, which functions as the axis of the inner tube 3 when the inner tube 3 rotates.

As shown in FIGS. 13 and 14, the outer tube 2 is cylindrical (tubular) and has a certain diameter from its proximal portion to distal portion. As shown in FIGS. 15(a) and 15(b), the outer tube 2 has a three-layer construction composed of an inner layer 21, an intermediate layer 22 formed on the periphery of the inner layer 21, and an outer layer 23 formed on the periphery of the intermediate layer 22. The outer tube 2 is flexible so that it is capable of curving freely along a curve of the blood vessel when the outer tube 2 is inserted thereinto.

The dimension of the outer tube 2 is not specifically limited, but it is preferable to set the outer diameter (diameter) thereof to 1.5 to 3.5 mm, the inner diameter (diameter) thereof to 1.0 to 3.0 mm, and the axial length thereof to 30 to 150 cm.

It is preferable that the inner layer 21 of the outer tube 2 is composed of a low-frictional material. As a material composing the inner layer 21, for example, fluorinated resins such as polytetrafluoroethylene are used.

It is preferable that the intermediate layer 22 of the outer tube 2 has a composition functioning as a reinforcing material. As a material composing the intermediate layer 22, it is possible to list stainless steel, tungsten, nickel, titanium, nickel titanium alloy, nickel cobalt alloy, nickel manganese alloy, and carbon fiber. It is preferable that the intermediate layer 22 is composed of a mesh composed of knitted metal wires of the above-described metals or knitted fibers of carbon fibers or the like.

As a material composing the outer layer 23 of the outer tube 2, it is possible to use the following: polyolefins such as polyethylene, polypropylene, polybutadiene; polyvinyl chloride, polyurethane, polyether polyurethane, ethylene-vinyl acetate copolymer, polyethylene terephthalate, polybutylene terephthalate, polyamide, polyether polyamide, polyester polyamide; thermoplastic elastomers such as styrene, polyolefins, polyurethanes, polyesters, polyamides, polybutadienes, trans-polyisoprenes, fluororubbers, and chlorinated polyethylenes. It is possible to use mixtures of not less than two kinds of these thermoplastic and thermoplastic elastomers or laminates of not less than two kinds thereof.

In removing the occlusive material in the blood vessel, it is preferable to enhance the X-ray opaque of the outer tube 2 at essentially the distal portion thereof so that the distal portion thereof is visible in an examination by fluoroscopy. In this case, it is preferable to add an X-ray-opaque material such as barium sulfate, platinum, gold, tungsten or the like to the above-described material composing the outer layer 23 or provide the distal portion of the outer tube 2 with an X-ray opaque portion composed of the X-ray-opaque material. In the embodiment, as shown in FIGS. 13 and 14, the outer tube 2 is provided with an X-ray opaque portion (marker) 24 at its distal portion.

As shown in FIGS. 15(a) and 15(b), the inner tube 3 is cylindrical (tubular) and has an outer diameter so set that it can be inserted into the outer tube 2. A first passage X is formed between the periphery of the inner tube 3 and the inner periphery of the outer tube 2. The inner tube 3 is also flexible.

As a material composing the inner tube 3, it is possible to list polyesters such as polyether ether ketone, polyethylene terephthalate, and polybutylene terephthalate; polyimide, polyamide, polyether polyamide, polyester polyamide, ABS resin, AS resin, and fluorinated resins such polytetrafluoroethylene. It is possible to use mixtures of not less than two kinds of these materials or laminates of not less than two kinds thereof.

The dimension of the inner tube 3 is not restricted to a specific value, but it is preferable to set the outer diameter (diameter) thereof to 0.8 to 1.8 mm, the inner diameter (diameter) thereof to 0.5 to 1.5 mm, and the axial length thereof to 50 to 170 cm.

As shown in FIG. 13, the first and second removing members 5a and 5b for drilling and removing the occlusive material formed in the blood vessel are fixed to the distal portion of the inner tube 3 having the above-described construction.

As shown in FIG. 16, the first and second removing members 5a and 5b are capable of taking a contracted state (narrowed state) in which they are accommodated in the outer tube 2 (accommodated state) and a developed state in which the first and second removing members 5a and 5b project from the distal portion of the outer tube 2 and radially expand owing to an elastic restoring force thereof, with the distal end thereof unfolding, as shown in FIG. 17. The first and second removing members 5a and 5b take a natural state (state in which no load is applied) respectively in the developed state. In the developed state, the distal portion of each of the first and second removing members 5a and 5b moves away from the guide member 6. In removing the occlusive material, the first and second removing members 5a and 5b project from the distal portion of the outer tube 2 and radially expand owing to the elastic restoring force thereof, thus having the developed state in which the distal end thereof unfolds. In the developed state, the distal end of the first removing member 5a projects from the distal end of the second removing member 5b. In this atherectomy catheter 10, the distal end of the first removing member 5a projects from the distal end of the second removing member 5b in the contracted state (the narrowed state, the accommodated state).

The first and second removing members 5a and 5b at the time when they have the developed state is described below representatively.

As shown in FIGS. 16 and 17, each of the first and second removing members 5a and 5b is thin and approximately cylindrical (approximately conic). Each of the first and second removing members 5a and 5b has at the distal portion thereof a plurality of projected portions 51 projected circumferentially toward the distal side of the catheter 10. Thereby the first and second removing members 5a and 5b are capable of easily and securely drilling the occlusive material.

A side-wall portion of each of the first and second removing members 5a and 5b is reticulate. More specifically, each of the first and second removing members 5a and 5b has a plurality of open portions 53 on a side surface (side wall) thereof. Thereby it is possible to discharge the occlusive material drilled by the first and second removing members 5a and 5b through the open portions 53 and inject a predetermined fluid to the blood vessel through the open portions 53.

The ratio of the area of the open portions 53 of the first removing member 5a to that of the side surface thereof is set to favorably 4 to 97% and more favorably 20 to 70%. Similarly, the ratio of the area of the open portions 53 of the second removing member 5b to that of the side surface thereof is also set to favorably 4 to 97% and more favorably 20 to 70%.

When the above-described ratio is less than the above-described lower limit value, there is a possibility that the first and second removing members 5a and 5b are incapable of expanding by themselves in dependence on other conditions.

When the above-described ratio is more than the above-described upper limit value, each of the first and second removing members 5a and 5b may twist or change from the developed state to the contracted state at the time of drilling in dependence on other conditions.

The ratio of the area of the open portions 53 of the first removing member 5a to that of the side surface thereof may be set equally to or differently from the ratio of the area of the open portions 53 of the second removing member 5b to that of the side surface thereof.

Each of the open portions 53 is approximately rhombic and thus has a pair of corners in its axial direction. When the first and second removing members 5a and 5b are accommodated in the outer tube 2 and thus have the contracted state, each of the open portions 53 so deforms that the angle of a pair of the axial corners thereof becomes small, whereas the angle of another pair of the corners (a pair of corners approximately vertical to the axial direction) thereof becomes large.

When the first and second removing members 5a and 5b project from the distal portion of the outer tube 2, each of the rhombic open portions 53 so deforms that the angle of a pair of the axial corners thereof becomes larger than the angle at the time when the first and second removing members 5a and 5b have the contracted state, whereas the angle of the another pair of the corners thereof becomes smaller than the angle at the time when the first and second removing members 5a and 5b have the contracted state. Therefore the first and second removing members 5a and 5b expand radially, thus having the developed state in which the distal end thereof unfolds (the first and second removing members 5a and 5b return to the natural state).

Owing to the above-described construction, each of the first and second removing members 5a and 5b is capable of taking the developed state smoothly and reliably. The projected portion 51 of each of the first and second removing members 5a and 5b disposed at the distal portion thereof is pointed like the top of a mountain (V-shaped).

As a material composing the first and second removing members 5a and 5b, it is preferable to use shape memory alloys. In this case, a part of the material may be composed of the shape memory alloys. As the shape memory alloys, the following can be used: Ti—Ni-based alloys such as Ti—Ni, Ti—Ni—Cu, and the like; a Cu-based alloys such as Cu—Al—Mn, Cu—Al—Ni, and the like; Fe-based alloys such as Fe—Mn—Si and the like; Cd-based alloys such as Au—Cd, Ag—Cd, and the like; ferromagnetic shape memory alloys such as Ni—Mn—Ga alloy, and Fe—Pd alloy.

The material composing the first removing member 5a and that composing the second removing member 5b may be identical to or different from each other.

The first and second removing members 5a and 5b are concentric (approximately coaxial) with the axis of the inner tube 3, with the first removing member 5a disposed inward (the side of the guide member 6) from the second removing member 5b. More specifically, the first removing member 5a is disposed at the inner peripheral side, while the second removing member 5b is disposed at the peripheral side.

Therefore the diameter of the first removing member 5a is set smaller than that of the second removing member 5b. The outer diameter of the distal portion of the first removing member 5a is also set smaller than that of the distal portion of the second removing member 5b.

In this case, the outer diameter of the distal portion of the first removing member 5a is set to favorably 25 to 65% and more favorably 30 to 60% of that of the distal portion of the second removing member 5b. Thereby the occlusive material can be drilled and removed easily and securely.

The axial position of the distal end (distal end surface) of the first removing member 5a is located nearer to the distal side of the atherectomy catheter than that of the distal end of the second removing member 5b. Therefore the first removing member 5a drills the occlusive material in advance of the second removing member 5b. Afterwards, the second removing member 5b drills it. The distal side of the first removing member 5a projects favorably 1 to 10 mm and more favorably 3 to 6 mm from the distal end of the second removing member 5b. Thereby the occlusive material can be drilled and removed easily and securely.

In the present invention, the axial position of the distal end of the first removing member 5a may be almost coincident with that of the distal end of the second removing member 5b. In this case, the first and second removing members 5a and 5b drill the occlusive material almost simultaneously.

It is preferable that the outer diameter of the distal portion of the first removing member 5a or/and the second removing member 5b gradually decreases toward the distal end thereof. In the example shown in the drawings, a favorable mode is shown. That is, the outer diameter of the distal portion of the first removing member 5a and that of the distal portion of the second removing member 5b gradually decrease toward the distal end thereof. Thereby the occlusive material can be drilled and removed easily and securely.

The dimension of each of the first and second removing members 5a and 5b is not specifically restricted but appropriately set according to an object, a portion to which they are applied, a material, and various conditions. But it is preferable to set the dimension of each of the first and second removing members 5a and 5b in the following ranges.

The thickness of the first removing member 5a is set to preferably 0.1 to 0.3 mm.

The outer diameter (diameter) of the distal end of the first removing member 5a is set to preferably 1 to 3 mm. The outer diameter (diameter) of the first removing member 5a in the vicinity of the middle portion is set to preferably 2 to 4 mm.

The axial length of the first removing member 5a is set to preferably 15 to 45 mm.

The thickness of the second removing member 5b is set to preferably 0.1 to 0.3 mm.

The outer diameter (diameter) of the second removing member 5b is set to a value corresponding to the inner diameter of the blood vessel. That is, the outer diameter (diameter) of the distal end of the second removing member 5b is set to preferably 3 to 6 mm. The outer diameter (diameter) of the second removing member 5b in the vicinity of the middle portion is set to preferably 5 to 10 mm.

The axial length of the second removing member 5b is set to preferably 10 to 40 mm.

The method of fixing (sticking) the first and second removing members 5a and 5b to the distal portion of the inner tube 3 is not specifically restricted. The first and second removing members 5a and 5b can be fixed to the distal portion of the inner tube 3 as follows:

Initially the first removing member 5a is fixed to the distal portion of the inner tube 3.

As shown in FIG. 19, the inner tube 3 having a ring-shaped convex portion (first convex portion) 31a provided on the periphery of the distal portion thereof is prepared. In this case, after photo-curing resin is applied to the periphery of the distal portion of the inner tube 3, the photo-curing resin is cured to form the convex portion 31a.

A tubular member (first tubular member) 55a, shown in FIG. 18, which is to be mounted around the inner tube 3 is prepared. The inner diameter (diameter) of the tubular member 55a is set less than a value obtained by adding a value twice as large as the thickness of the first removing member 5a to the outer diameter (diameter) of the convex portion 31a. Stainless steel or the like is used as a material composing the tubular member 55a.

As shown in FIG. 20, after the first removing member 5a is inserted into the tubular member 55a by narrowing the proximal portion of the first removing member 5a, the proximal side of the inner tube 3 is inserted into the distal side of the first removing member 5a and the tubular member 55a. Thereafter the movement of the tubular member 55a is stopped by bringing it into contact with the inner side of the proximal portion of the first removing member 5a narrowed by the tubular member 55a. The tubular member 55a is disposed nearer to the proximal side of the atherectomy catheter 10 than the convex portion 31a formed around the inner tube 3. Thereby the tubular member 55a is placed at a position of the periphery of the inner tube 3 nearer to the proximal side of the atherectomy catheter 10 than the convex portion 31a formed around the inner tube 3, with the proximal portion of the first removing member 5a disposed between the periphery of the inner tube 3 and the inner periphery of the tubular member 55a.

After the proximal end of the first removing member 5a is projected toward the proximal side of the catheter 10 in a predetermined length from the proximal end of the tubular member 55a, a tube 56a is mounted around the proximal portion of the first removing member 5a. Various resin materials are used as a material composing the tube 56a.

After a photo-curing resin 57a is supplied to the periphery of the inner tube 3 from the proximal side of the tube 56a toward the distal side thereof and cured, the tubular member 55a and an end of the first removing member 5a are fixed to the inner tube 3. Thereafter the photo-curing resin 57a is applied to the inner tube 3 to fill a level difference between an end of the tube 56a and the inner tube 3 and is cured. By fixing the tubular member 55a to the periphery of the inner tube 3 with the photo-curing resin (adhesive agent) 57a, the first removing member 5a is fixed to the inner tube 3.

The proximal portion of the first removing member 5a is caulked in cooperation of the convex portion Ma, the tubular member 55a, the tube 56a, and the photo-curing resin 57a to firmly fix the first removing member 5a to the inner tube 3, as in the case of a convex portion 31b which will be described below.

Thereafter similarly to the method of fixing the first removing member 5a to the inner tube 3, the second removing member 5b is fixed to the distal portion of the inner tube 3.

As shown in FIG. 21, initially a ring-shaped convex portion (second convex portion) 31b is formed on the periphery of the distal portion of the inner tube 3. In this case, after photo-curing resin is applied to the periphery of the distal portion of the inner tube 3, the photo-curing resin is cured to form the convex portion 31b. The convex portion 31b is disposed nearer to the proximal side of the atherectomy catheter 10 than the proximal portion (photo-curing resin 57a) of the tube 56a. It is preferable to set the distance between the proximal end of the tube 56a and the distal end of the convex portion 31b to 3 to 10 mm.

A tubular member (second tubular member) 55b, shown in FIG. 18, which is to be mounted around the inner tube 3 is prepared. The inner diameter (diameter) of the tubular member 55b is set less than a value obtained by adding a value twice as large as the thickness of the second removing member 5b to the outer diameter (diameter) of the convex portion 31b. Stainless steel or the like is used as a material composing the tubular member 55b.

As shown in FIG. 22, after the second removing member 5b is inserted into the tubular member 55b by narrowing the proximal portion of the second removing member 5b, the proximal side of the inner tube 3 is inserted into the distal side of the second removing member 5b and the tubular member 55b. Thereafter the movement of the tubular member 55b is stopped by bringing it into contact with the inner side of the proximal portion of the second removing member 5b narrowed by the tubular member 55b. The tubular member 55b is disposed nearer to the proximal side of the atherectomy catheter 10 than the convex portion 31b formed around the inner tube 3. Thereby the tubular member 55b is placed at a position of the periphery of the inner tube 3 nearer to the proximal side of the atherectomy catheter 10 than the convex portion 31b formed around the inner tube 3, with the proximal portion of the second removing member 5b disposed between the periphery of the inner tube 3 and the inner periphery of the tubular member 55b.

After the proximal end of the second removing member 5b is projected toward the proximal side of the catheter 10 in a predetermined length from the proximal end of the tubular member 55b, a tube 56b is mounted around the proximal portion of the second removing member 5b. Various resin materials are used as a material composing the tube 56b.

After a photo-curing resin 57b is supplied to the periphery of the inner tube 3 from the proximal side of the tube 56b toward the distal side thereof and is cured, the tubular member 55b and an end of the first removing member 5b are fixed to the inner tube 3. Thereafter the photo-curing resin 57b is applied to the inner tube 3 to fill a level difference between an end of the tube 56b and the inner tube 3 and is cured. By fixing the tubular member 55b to the periphery of the inner tube 3 with the photo-curing resin (adhesive agent) 57b, the second removing member 5b is fixed to the inner tube 3. The second removing member 5b is disposed at the peripheral side of the first removing member.

The first removing member 5a may be fixed (stuck) to the distal portion of the inner tube 3 by caulking the tubular member 55a. Similarly the second removing member 5b may be fixed (stuck) to the distal portion of the inner tube 3 by caulking the tubular member 55b.

As shown in FIG. 16, as a rotation-assisting means, a pipe (inner tube-reinforcing member) 71 is mounted around the proximal portion of the inner tube 3. Thereby the rotation torque transmitting performance at the proximal portion of the inner tube 3 is made larger than that at the distal portion thereof. Thus the inner tube 3 and the first and second removing members 5a and 5b can be rotated easily about the axis inside the outer tube 2. Metal materials such as stainless steel are used as a material composing the pipe 71.

The rotation-assisting means does not necessarily have to be constructed of the pipe 71, but may be realized by composing the proximal portion of the inner tube 3 of a metal material such as stainless steel.

An inner-tube hub 72 is provided at the proximal end (proximal portion) of the inner tube 3. The inner-tube hub 72 is provided with a hole (not shown) formed along the axis thereof and a gripping portion 73 formed flatly on the side surface thereof so that the inner-tube hub 72 can be rotated with fingers. Further the inner-tube hub 72 is provided with a coupling portion 74 formed at the proximal side thereof.

As shown in FIG. 14, the connector 4 disposed at the proximal portion of the outer tube 2 is a Y-connector having a port 4A. The first passage X (see FIGS. 15(a) and 15(b)) is formed between the inner periphery of the connector 4 and the periphery of the inner tube 3. That is, the port 4A communicates with the first passage X. The connector 4 is coupled with the proximal portion of the outer tube 2 by tightening a fastening member 20.

Similarly to the above-described valve and the plunger shown in FIG. 9, a ring-shaped valve 41 is mounted at an inner side of the proximal portion of the connector 4. The connector 4 is provided with a plunger (operation portion) 42 axially movable at the proximal side thereof. The valve 41 and the plunger 42 are the same as those described previously.

Similarly to the guide member 6 shown in FIG. 10, the guide member 6 is flexible and long. That is, the guide member 6 is flexible and linear. In removing the occlusive material, the guide member 6 projects in a predetermined length from the distal portion of the first and second removing members 5a and 5b. The position of the occlusive material can be specified by striking the guide member 6 against the occlusive material. Further the distal portion of the guide member 6 is pierced into the center of the occlusive material to utilize the guide member 6 as the axis in the rotation of the inner tube 3 and the first and second removing members 5a and 5b. Thereby it is possible to suppress whirling of the rotational axis of the first and second removing members 5a and 5b, prevent the wall of the blood vessel from being damaged, and securely remove the occlusive material.

The same guide member 6 as that described above is used. As shown in FIGS. 13 and 17, the guide member 6 is removable from the inner tube 3. The guide member 6 is provided with a guide hub 63 at its proximal portion. As shown in FIGS. 13 and 17, the guide member 6 is fixedly mounted on the inner tube 3 by inserting the guide member 6 into the inner tube 3 and fitting the guide hub 63 on the coupling portion 74 of the inner-tube hub 72 of the inner tube 3.

The distal side of the guide member 6 projects in a predetermined length from the distal end of the first removing member 5a (distal end of first removing member 5a or second removing member 5b disposed at distal side), when the guide member 6 is mounted on the inner tube 3, with the guide hub 63 fitting on the coupling portion 74 of the inner-tube hub 72. The predetermined projected length of the guide member 6 is favorably 1 to 8 mm and more favorably 2 to 5 mm.

By setting the predetermined projected length of the distal side of the guide member 6 to the above-described range, it is possible to keep the guide member 6 safe and securely function the guide member 6 as the axis of the inner tube 3 and the first and second removing members 5a and 5b when they rotate.

As shown in FIG. 15(d), a lumen 64 is formed inside the guide hub 63. The lumen 64 is approximately semicircular in its cross-sectional configuration and axially penetrates therethrough. When the guide hub 63 fits on the inner-tube hub 72 of the inner tube 3, the lumen of the inner tube 3, that of the inner-tube hub 72, and the lumen 64 of the guide hub 63 communicate with one another to form a second passage Y.

A coupling portion 65 is provided at the proximal portion of the guide hub 63.

The atherectomy catheter 10 has connectable rotation-assisting device 8 for rotating the inner tube 3, the first removing member 5a, the second removing member 5b, and the guide member 6. The rotation-assisting device 8 can be connected with the coupling portion 65 of the guide hub 63.

It is possible to discharge a fluid containing the occlusive material drilled by the first and second removing members 5a and 5b to the outside of a human body through the first passage X and inject a predetermined fluid into the blood vessel through the second passage Y.

In this case, a discharge portion 91 of an injection and discharge apparatus (injection and discharge means) 9 is connected with the port 4A of the connector 4. An injection portion 92 of the injection and discharge apparatus 9 is connected with the coupling portion 65 of the guide hub 63 through the rotation-assisting device 8. In this construction, the fluid containing the occlusive material is sucked through the discharge portion 91 and discarded (discharged) from the discharge port 93. The injection portion 92 injects the fluid contained in a reserve container 95 connected with an injection port 94 into the blood vessel.

The fluid containing the occlusive material drilled by the first and second removing members 5a and 5b is aspirated and discharged by the operation (drive) of the discharge portion 91 of the injection and discharge apparatus 9. At the time of the aspirating and discharge, it is possible to adjust the flow rate of the fluid, namely, the flow rate per unit time.

The predetermined fluid is injected to the blood vessel by the operation (drive) of the injection portion 92 of the injection and discharge apparatus 9. At the time of the injection, it is possible to adjust the flow rate of the fluid, namely, the flow rate per unit time.

The operation (one example of method of using atherectomy catheter 10) of the atherectomy catheter 10 is described below.

In performing treatment of removing the occlusive material in the blood vessel, the inner tube 3 to which the first and second removing members 5a and 5b have been fixed is inserted into the outer tube 2 and accommodated therein at the distal side thereof, with the diameter of each of the first and second removing members 5a and 5b decreased. The inner tube 3 and the outer tube 2 are inserted into the blood vessel until the inner tube 3 and the outer tube 2 reach a desired portion inside the blood vessel by operating a guide wire (not shown) through a sheath (not shown). The situation at that time is monitored by using fluoroscopy or the like.

When the inner tube 3 and the outer tube 2 have reached the desired portion inside the blood vessel, the guide wire is pulled out of the blood vessel. Thereafter the guide member 6 is inserted into the inner tube 3 from the distal end thereof to fit the guide hub 63 of the guide member 6 on the inner-tube hub 72. Thereby the guide member 6 is fixed to the inner tube 3.

Thereafter the plunger 42 of the connector 4 is rotated to loosen the valve 41. In this state, the inner tube 3 is pressed toward the distal side of the outer tube 2 (alternatively the outer tube 2 is drawn toward the proximal side of the inner tube 3). Thereby as shown in FIG. 23, the first and second removing members 5a and 5b project from the distal portion of the outer tube 2 and expand radially owing to the elastic restoring force thereof, thus having the developed state in which the distal end of each of the first and second removing members 5a and 5b unfolds. At this time, the guide member 6 projects in a predetermined length from the distal end of the first removing member 5a. Thereafter the entire atherectomy catheter 10 is moved toward the distal side thereof to move the guide member 6 forward so that the distal portion thereof is pierced into the occlusive material (lesion) H. Thereafter the plunger 42 of the connector 4 is rotated to tighten the valve 41 inward so that the inner tube 3 is rotatably fixed to the outer tube 2.

Thereafter as shown in FIG. 24(a), the inner tube 3 is rotated about the guide member 6 functioning as the axis thereof, with the atherectomy catheter 10 being entirely moved to the distal side thereof (moved forward). Thereby the first and second removing members 5a and 5b move to the distal side of the catheter 10, with the first and second removing members 5a and 5b rotating about the guide member 6 functioning as the axis thereof.

Thereby as shown in FIG. 24(b), as the removing member 6, the first removing member 5a, and the second removing member 5b enter the occlusive material H, the occlusive material H is drilled by the projected portion 51 of the first and second removing members 5a and 5b disposed at the distal portion thereof.

At this time, the first removing member 5a having the smaller diameter drills the occlusive material in advance of the second removing member 5b. Thereby a hole having an inner diameter (size) corresponding to the outer diameter of the first removing member 5a is formed in the occlusive material H. Subsequently to the first removing member 5a (thereafter), the second removing member 5b having the larger diameter drills a remaining part of the occlusive material H which has become tubular, thus enlarging the hole. In this manner, blood is capable of flowing through the blood vessel closed with the occlusive material H.

When the occlusive material H is removed by only a large-diameter removing member corresponding to the second removing member 5b, a comparatively large load is applied to the large-diameter removing member. But in the atherectomy catheter 10, the outer diameter of the first removing member 5a is comparatively small. Thus a comparatively small load is applied to the first removing member 5a. Because the second removing member 5b only enlarges the hole formed by the first removing member 5a, a comparatively small load is also applied to the second removing member 5b. Thereby it is possible to prevent twist of the first and second removing members 5a and 5b and hence fluctuation of a position to be drilled and the diameter thereof. Thereby it is possible to drill the occlusive material H smoothly and securely.

Owing to the forward movement and rotation of the guide member 6 and the first and second removing members 5a and 5b, as shown in FIG. 24(c), the first and second removing members 5a and 5b are securely capable of removing the occlusive material H. In this case, even though the occlusive material H is a hard atheroma such as calcified lesion generated in the blood vessel, the occlusive material H can be securely drilled and removed.

The removed occlusive material H is discharged to the outside through the first passage X.

As described above, according to the atherectomy catheter 10, the first and second removing members 5a and 5b are moved to the lesion of the blood vessel. Thereafter the first and second removing members 5a and 5b are moved to the distal side of the catheter 10, with the first and second removing members 5a and 5b being rotated. Thereby atherectomy catheter 10 gradually drills and removes the occlusive material H at the projected portion 51 of the first and second removing members 5a and 5b thereof. Therefore the atherectomy catheter 10 is capable of drilling and removing the occlusive material H easily, rapidly, securely, and safely.

Further because the first and second removing members 5a and 5b rotate about the guide member 6 functioning as the axis thereof, they can be rotated easily, securely, and stably.

The atherectomy catheter 10 has the small-diameter first removing member 5a and the large-diameter second removing member 5b disposed coaxially therewith. It is hitherto necessary to separately perform an operation of drilling and removing the occlusive material by using two atherectomy catheters having the large-diameter removing member and the small-diameter removing member. On the other hand, the atherectomy catheter of the present invention allows the operation of drilling and removing the occlusive material to be performed once. Therefore the atherectomy catheter 10 is capable of removing the occlusive material H in a shorter period of time than the conventional atherectomy catheter.

As described above, unlike the conventional art, the atherectomy catheter 10 of the embodiment eliminates the need for searching a lesion for an actual lumen by using the guide wire, piercing the guide wire into the lesion, and repeatedly moving the sheath (shear member) back and forth. Therefore without damaging or breaking through the blood vessel and without requiring skill, the occlusive material H can be removed easily, rapidly, securely, and safely. Further the atherectomy catheter 10 is capable of decreasing burden to be imposed on an operator and a patient.

Furthermore because the drilled occlusive material H is discharged to the outside through the first passage X, the atherectomy catheter 10 is very safe.

In removing the occlusive material H, the drilled occlusive material H is discharged to the outside through the first passage X. In addition, physiologic saline or the like can be injected into the blood vessel from the second passage Y. This construction allows the removal of the occlusive material H to be continued without contracting or deforming the blood vessel by a pressure difference generated by aspirating of the drilled occlusive material H in discharging the occlusive material H to the outside.

Because the occlusive material H can be removed in the above-described manner, it is possible to recanalise the blood vessel and form a way for a device to be used subsequently to the atherectomy catheter 10. In addition, it is possible to perform a subsequent treatment step (expansion of blood vessel with balloon, stent, and the like).

The present invention is not limited to the above-described embodiment of the atherectomy catheter described with reference to the drawings. The construction of each part can be replaced with arbitrary constructions having functions similar thereto. In addition, other arbitrary component parts can be added to the present invention.

In the present invention, as the member (removing member) for removing the occlusive material, the atherectomy catheter has at least the first removing member and the second removing member. That is, the number of the removing members is not limited to two but may be not less than three.

Portions from which the occlusive materials are removed by the atherectomy catheter of the present invention include the bile duct, the urethra, and the like in addition to the blood vessel.

The occlusive material includes a thrombus, a fatty plaque, an arteriosclerotic layer, a calculus, and the like.

According to the atherectomy catheter of this embodiment in removing the occlusive material, the first and second removing members expand radially and have the developed state in which the distal end thereof unfold. Thus by rotating the first and second removing members with the first and second removing members moving forward, it is possible to drill and remove the occlusive material stenosing or occluding the lumen of the tubular organ (for example, blood vessel) easily, rapidly, securely, and safely.

When the atherectomy catheter has the long flexible guide member, mounted on the inner tube in penetration therethrough, which functions as the axis of the inner tube 3 when the inner tube 3 rotates, the first and second removing members rotate about the guide member functioning as the axis thereof. Thus the first and second removing members can be rotated easily, securely, and stably. Further the occlusive material can be removed easily and securely.

The atherectomy catheter has the first and second removing members. Thus it is hitherto necessary to perform the operation of drilling and removing the occlusive material twice by using two atherectomy catheters having different diameters. On the other hand, the atherectomy catheter of the present invention allows the operation of drilling and removing the occlusive material to be performed once. Therefore the atherectomy catheter of the present invention is capable of removing the occlusive material in a shorter period of time than the conventional atherectomy catheter.

As described above, unlike the conventional art, the atherectomy catheter of the embodiment eliminates the need for searching a lesion for an actual lumen by using the guide wire, piercing the guide wire into the lesion, and repeatedly moving the sheath (shear member) back and forth. Therefore without damaging or breaking through the tubular organ and without requiring skill, the occlusive material can be removed easily, rapidly, securely, and safely. Further the atherectomy catheter is capable of decreasing burden to be imposed on an operator and a patient.

What is claimed is:

1. An atherectomy catheter comprising:
   a flexible outer tube;
   a flexible inner tube which is inserted into said outer tube rotatably about an axis thereof and axially movable;
   first and second removing members fixed to a distal portion of said inner tube and accommodated in said outer tube to drill and remove an occlusive material which stenoses or occludes a lumen of a tubular organ,
   wherein said first and second removing members project from a distal portion of said outer tube and radially expand, thus having a developed state in which a distal end of each of said first and second removing members unfolds;
   first and second convex portions formed on a periphery of said distal portion of said inner tube and first and second tubular members into which said distal portion of said inner tube is inserted;
   wherein said distal portion of said inner tube is inserted into said first tubular member with said first tubular member disposed nearer to a proximal side of said atherectomy catheter than said first convex portion formed on said inner tube, and said first tubular member is fixed to said periphery of said inner tube with a proximal portion of said first removing member disposed between said periphery of said inner tube and an inner periphery of said first tubular member, whereby said first removing member is fixed to said inner tube; and
   said distal portion of said inner tube is inserted into said second tubular member with said second tubular member disposed nearer to a proximal side of said atherectomy catheter than said second convex portion formed on said inner tube, and said second tubular member is fixed to said periphery of said inner tube with a proximal portion of said second removing member disposed between said periphery of said inner tube and an inner periphery of said second tubular member, whereby said second removing member is fixed to said inner tube.

2. An atherectomy catheter according to claim 1, wherein said first removing member is thin and approximately cylindrical and has a plurality of projected portions projected toward a distal end of said atherectomy catheter at said distal portion thereof, with said projected portions circumferentially disposed; and said second removing member is thin and approximately cylindrical and has a plurality of projected portions projected toward a distal end of said catheter at said distal portion thereof, with said projected portions circumferentially disposed.

3. An atherectomy catheter according to claim 1, wherein said first and second removing members are concentric with said axis of said inner tube; and said first removing member is disposed inward from said second removing member.

4. An atherectomy catheter according to claim 3, wherein in said developed state, said distal end of said first removing member projects from said distal end of said second removing member.

5. An atherectomy catheter according to claim 1, wherein in said developed state, an outer diameter at said distal portion of said first removing member or an outer diameter at said distal portion of said second removing member gradually decreases to said distal end thereof.

6. An atherectomy catheter according to claim 1, further comprising a fixing means for preventing an axial movement of said inner tube with respect to said outer tube.

7. An atherectomy catheter according to claim 6, wherein when an axial movement of said inner tube is fixed, said fixing means has a function of permitting a rotation of said inner tube about an axis thereof with respect to said outer tube and interrupting a passage of a fluid through a first passage formed between an inner periphery of said outer tube and a periphery of said inner tube.

8. An atherectomy catheter according to claim 1, wherein said inner tube has at a proximal portion thereof a rotation-assisting means for making a rotation torque transmitting performance at said proximal portion thereof larger than a rotation torque transmitting performance at a distal portion thereof.

9. An atherectomy catheter according to claim 1, further comprising a guide member, removably mounted on said inner tube in penetration therethrough, which functions as an axis of said inner tube when said inner tube rotates, a hub at said proximal portion of said inner tube, a hub at a proximal portion of said guide member, the hub of the guide member being fittable on said hub of the inner tube, said guide member is composed of super-elastic alloy, stainless steel or resin, and a distal side of said guide member projects distally 1 to 8 mm beyond a distal end of said removing member when said hub of said inner tube fits on said hub of said guide member.

10. An atherectomy catheter according to claim 9, further comprising a rotation-assisting device for rotating said inner tube and said first and second removing members, and wherein said rotation-assisting device is connectable with said hub of said guide member.

11. An atherectomy catheter according to claim 1, wherein a fluid containing said occlusive material drilled by said first and second removing members can be discharged outside a human body through a first passage formed between said inner periphery of said outer tube and said periphery of said inner tube.

12. An atherectomy catheter according to claim 11, wherein a fluid can be injected into a tubular organ through a second passage, a part of which is formed of a lumen of said inner tube.

13. An atherectomy catheter according to claim 12, further comprising an injection and discharge means for discharging a fluid through said first passage, adjusting a flow rate of said fluid, injecting a fluid into said tubular organ through said second passage, and adjusting a flow rate of said fluid.

* * * * *

UNITED STATES PATENT AND TRADEMARK OFFICE
CERTIFICATE OF CORRECTION

| | | |
|---|---|---|
| PATENT NO. | : 7,833,240 B2 | Page 1 of 1 |
| APPLICATION NO. | : 11/714148 | |
| DATED | : November 16, 2010 | |
| INVENTOR(S) | : Naohisa Okushi et al. | |

It is certified that error appears in the above-identified patent and that said Letters Patent is hereby corrected as shown below:

Column 8, Line 65: Change "tuba." to -- tube 2. --.

Column 10, Line 21: Change "lime" to -- time --.

Signed and Sealed this
Eighth Day of March, 2011

David J. Kappos
*Director of the United States Patent and Trademark Office*